＊US007183090B2

(12) United States Patent
Kruus et al.

(10) Patent No.: US 7,183,090 B2
(45) Date of Patent: Feb. 27, 2007

(54) LACCASE ENZYME AND THE GENE ENCODING THE ENZYME

(75) Inventors: Kristiina Kruus, Espoo (FI); Laura-Leena Kiiskinen, Espoo (FI); Marjaana Rättö, Vantaa (FI); Liisa Viikari, Helsinki (FI); Markku Saloheimo, Helsinki (FI)

(73) Assignee: Valtion Teknillinen Tutkimuskeskus (FI)

( * ) Notice: Subject to any disclaimer, the term of this patent is extended or adjusted under 35 U.S.C. 154(b) by 474 days.

(21) Appl. No.: 10/296,325

(22) PCT Filed: May 23, 2001

(86) PCT No.: PCT/FI01/00503

§ 371 (c)(1),
(2), (4) Date: Nov. 22, 2002

(87) PCT Pub. No.: WO01/92498

PCT Pub. Date: Dec. 6, 2001

(65) Prior Publication Data

US 2005/0089980 A1    Apr. 28, 2005

(30) Foreign Application Priority Data

May 23, 2000  (FI) ................................. 20001240

(51) Int. Cl.
*C12N 9/02*    (2006.01)
*C07H 21/04*   (2006.01)

(52) U.S. Cl. ..................................... 435/189; 536/23.2
(58) Field of Classification Search ................. 435/189
See application file for complete search history.

(56) References Cited

U.S. PATENT DOCUMENTS

| 5,691,193 A | 11/1997 | Paice et al. |
| 5,750,388 A | 5/1998 | Berka et al. |
| 5,770,418 A | 6/1998 | Yaver et al. |
| 5,795,760 A * | 8/1998 | Berka et al. ................. 435/189 |

FOREIGN PATENT DOCUMENTS

| DE | 41 37 761 A1 | 11/1992 |
| EP | 0 408 803 B1 | 1/1991 |
| EP | 0 852 260 A1 | 7/1998 |
| JP | 8-70861 A | 3/1996 |
| JP | 9-56378 A | 3/1997 |
| JP | 2984552 B2 | 11/1999 |
| JP | 2984584 B2 | 11/1999 |
| WO | WO 92/01046 A1 | 1/1992 |
| WO | WO 95/07988 A1 | 3/1995 |
| WO | WO 95/23232 A1 | 8/1995 |
| WO | WO 95/33837 A1 | 12/1995 |
| WO | WO 96/06930 A1 | 3/1996 |
| WO | WO 97/08325 A2 | 3/1997 |
| WO | WO 98/55628 A2 | 12/1998 |
| WO | WO 99/54545 A1 | 10/1999 |

OTHER PUBLICATIONS

Kiiskinen et al (2004) Applied and Environmental Microbiology, vol. 70 (1), pp. 137-144.*
Kiiskinen et al (2002) Applied Microbiology and Biotechnology, vol. 59 (2-3), pp. 198-204.*
Hakulinen et al (2002) Nature Structural Biology, vol. 9 (8), pp. 601-605.*
Berka et al., Applied and Environmental Microbiology, vol. 63, No. 8, pp. 3151-3157 (1997).
Farnet et al., Can. J. Microbiol., vol. 46, pp. 189-194 (2000).
Bharathi et al., J. Anim. Morphol. Physiol., vol. 40, Nos. 1 & 2, pp. 153-161 (1993).
Machuca et al., BIOSIS, vol. 27, No. 3, pp. 217-223 (1998) Abstract Only.
Stephen F. Altschul et al., *J. Mol. Biol.*, vol. 215, (1990), pp. 403-410.
Juan Fernandez-Larrea et al., *Mol. Gen. Genet.*, vol. 252, (1996), pp. 539-551.
Marion Heinzkill et al., *Applied and Environmental Microbiology*, vol. 64, No. 5, (May 1998), pp. 1601-1606.
Leif J. Jonsson et al., *Curr. Genet.*, vol. 32, (1997), pp. 425-430.
Yasushi Kojima et al., *The Journal of Biological Chemistry*, vol. 265, No. 25, (Sep. 5, 1990), pp. 15224-15230.
Marja-Leena Niku-Paavola et al., *Biochem. J.*, vol. 254, (1988), pp. 877-884.
Andrzej Paszczynski et al., *FEMS Microbiology Letters*, vol. 29, (1985), pp. 37-41.
U. Raeder et al., *Letters in Applied Microbiology*, vol. 1, (1985), pp. 17-20.
Markku Saloheimo et al., *Journal of General Microbiology*, vol. 137, (1991), pp. 1537-1544.
Markku Saloheimo et al., *BIO/TECHNOLOGY*, vol. 9, (Oct. 1991), pp. 987-990.
Debbie S. Yaver et al., *Applied and Environmental Microbiology*, vol. 62, No. 3, (Mar. 1996), pp. 834-841.
Kirsi Ravanko, *Screening of Thermostable laccase, Master's Thesis, Helsinki University of Technology*, (Oct. 15, 1996), 97 pages.
Grigorios Diamantidis et al., *Soil Biology & Biochemistry*, vol. 32, (2000), pp. 919-927.

* cited by examiner

*Primary Examiner*—Elizabeth Slobodyansky
(74) *Attorney, Agent, or Firm*—Birch, Stewart, Kolasch & Birch, LLP.

(57) ABSTRACT

The invention relates to a new laccase enzyme, which can be isolated from the strains of the *Melanocarpus* genus, the *M. albomyces* strain in particular. The pH optimum of the enzyme is within 5–8 and the enzyme works at a temperature of 30–80° C. The isoelectric point of the enzyme is about 4.0 as determined by isoelectric focusing and the molecular weight about 80 kDa, defined by SDS-PAGE. The enzyme is especially well suited to applications, wherein the pH and temperature conditions are high. The invention also relates to a gene that encodes laccase enzyme, and a laccase enzyme produced by recombinant technology.

9 Claims, 10 Drawing Sheets

```
atgaagacct tcaccagcgccct ggcgct cgt ggt gggcatgct tgccccgggt gccgt c
 M  K  T  F  T  S  A  L  A  L  V  V  G  M  L  A  P  G  A  V
gt tgccgcgcct cccagcact ccggcccagcgagat ct ggt cgagct gcgcgaggcgagg
 V  A  A  P  P  S  T  P  A  Q  R  D  L  V  E  L  R  E  A  R
caggagggcggcaaggacct ccgt ccccgt gagccgacgt gcaacacgccgagcaaccgg
 Q  E  G  G  K  D  L  R  P  R  E  P  T  C  N  T  P  S  N  R
gcgt gct ggagcgacggct t cgacat caacaccgact acgaagt cagcacgccggat acc
 A  C  W  S  D  G  F  D  I  N  T  D  Y  E  V  S  T  P  D  T
ggcgt cact cagt ct gtgagtcctcctctccgc
 G  V  T  Q  S ccccttggtttcgggaaggctgtccgaagggaaggaaagtccgaggctaactgcagacag tacgtattcaacctcactgaggttgacaactggatgggcccagacggcgtcgtcaaggag
 Y  V  F  N  L  T  E  V  D  N  W  M  G  P  D  G  V  V  K  E
aaggt gat gt t gat caat ggtgagtcgaccgcgaatgggatgtcgagttgccatccaaaa
 K  V  M  L  I  N tagacctgtgtaactgactggttcgatcacagggaacattatgggtacgtcttatctg
                                                G  N  I  M
gctgtcccggcacgccaatggcctttctttttccttgagcgtaggacgtgcgacggactga ctgagaacaataggccccaacatcgtcgcgaactggggtgatacggtcgaggtcaccgtg
          G  P  N  I  V  A  N  W  G  D  T  V  E  V  T  V
at caacaacct t gt gaccaacgga acgt cgat ccact ggcacggcat ccaccagaaggac
 I  N  N  L  V  T  N  G  T  S  I  H  W  H  G  I  H  Q  K  D
accaacct gcacgacggcgccaacggcgt gaccgagt gt ccgat cccgcccaagggcggc
 T  N  L  H  D  G  A  N  G  V  T  E  C  P  I  P  P  K  G  G
cagcggacgt accgct ggcgggcgcggcagt at ggcaccagct ggt accact cgcact t c
 Q  R  T  Y  R  W  R  A  R  Q  Y  G  T  S  W  Y  H  S  H  F
t cggcgcagt acggcaacggcgt ggt gggcacgat ccagat caacggcccggcgt cgct g
 S  A  Q  Y  G  N  G  V  V  G  T  I  Q  I  N  G  P  A  S  L
ccct acgacat cgacct t ggcgt gt t ccccat caccgact act accccggccgccgac
 P  Y  D  I  D  L  G  V  F  P  I  T  D  Y  Y  Y  R  A  A  D
gacct ggt gcact t cacgcagaacaacgcgccgccct t cagcgacaacgt gct cat caac
 D  L  V  H  F  T  Q  N  N  A  P  P  F  S  D  N  V  L  I  N
ggcacggccgt caacccgaacacgggcgagggccagt acgccaacgt gacgct gacgccg
 G  T  A  V  N  P  N  T  G  E  G  Q  Y  A  N  V  T  L  T  P
ggcaagcggcaccgcct gcgcat cct caacacgt cgaccgagaaccact t ccaggt gt cg
 G  K  R  H  R  L  R  I  L  N  T  S  T  E  N  H  F  Q  V  S
ct cgt caaccacaccat gacggt cat cgccgccgacat ggt gcccgt caacgccat gacg
 L  V  N  H  T  M  T  V  I  A  A  D  M  V  P  V  N  A  M  T
gt cgacagcct gt t cct ggccgt cggccagcgct acgacgt cgt cat cgacgcct cgaga
 V  D  S  L  F  L  A  V  G  Q  R  Y  D  V  V  I  D  A  S  R
gccccggacaact act ggt t caacgt cacct t t ggcggccaggcggcgt gcggcggct cg
 A  P  D  N  Y  W  F  N  V  T  F  G  G  Q  A  A  C  G  G  S
ct caacccgcacccggccgccat ct t ccact acgccggcgcgcccggcggcct gcccacc
 L  N  P  H  P  A  A  I  F  H  Y  A  G  A  P  G  G  L  P  T
gacgagggcacgccccccggt cgaccaccagt gcct ggacacgct cgacgt gcgccccgt c
 D  E  G  T  P  P  V  D  H  Q  C  L  D  T  L  D  V  R  P  V
gt gccgcgcagcgt gcccgt caacagct t cgt caagcggcccgacaacacgct gccggt g
 V  P  R  S  V  P  V  N  S  F  V  K  R  P  D  N  T  L  P  V
gcgct cgacct gaccggcacgcccct gt t cgt gt gg
 A  L  D  L  T  G  T  P  L  F  V  W
aaggt caacggcagcgacat caacgt cgact ggggcaagcccat cat cgact acat cct c
 K  V  N  G  S  D  I  N  V  D  W  G  K  P  I  I  D  Y  I  L
accggcaacaccagct acccccgt gt cggacaacat cgt gcaggt t gat gccgt cgat cag
 T  G  N  T  S  Y  P  V  S  D  N  I  V  Q  V  D  A  V  D  Q
```

Fig. 15

```
gtatgtcctctgttaaaccttacgtcgtacgattgcgctggcaaatcacacctcgtact gacgcaaaccaccacctcccttctagtggacatactggctcatcgagaacgatccggag
                            W  T  Y  W  L  I  E  N  D  P  E
ggcccctccagcctgccgcaccgatgcacctccac
 G  P  F  S  L  P  H  P  M  H  L  H
gtaagtggccaaccctgtcacgtac gttgcabccgccctctcccgggccccccaactcacacttcggactcccgtcccacagggc
                                                            G
cacgacttcctcgtgctggggcggtcgcccgacgtgccggcggcgtcgcagcagcgcttc
 H  D  F  L  V  L  G  R  S  P  D  V  P  A  A  S  Q  Q  R  F
gtgttcgactcggccgtggacctggcgcggctcaacggcgacaacccgccgcggcgcgac
 V  F  D  P  A  V  D  L  A  R  L  N  G  D  N  P  P  R  R  D
accacgatgctgccggccggcggctggctgctgctcgccttccgcaccgacaacccgggc
 T  T  M  L  P  A  G  G  W  L  L  A  F  R  T  D  N  P  G
gcctggctcttccactgccacatcgcctggcacgtgtcgggcggcctgtcggtcgacttc
 A  W  L  F  H  C  H  I  A  W  H  V  S  G  G  L  S  V  D  F
ctcgagcgccccgccgacctgcgccagcgcatctcccaggaggacgaggacgacttcaac
 L  E  R  P  A  D  L  R  Q  R  I  S  Q  E  D  E  D  D  F  N
cgcgtctgcgacgagtggcgcgcctactggccgacgaatccctaccccaagatcgactcg
 R  V  C  D  E  W  R  A  Y  W  P  T  N  P  Y  P  K  I  D  S
ggcctgaagcgtcgccgctgggtggaggagagcgagtggctggttcgttgatggggaaa
 G  L  K  R  R  R  W  V  E  E  S  E  W  L  V  R  -
ggggggtaggtgcgattcaggggtacctagggtgcacttgatgttgatgctcgatggag
aattggttttggttacttgttgttcactttcgacatgcgttggtccttgtttggattttt
taggttgtccagatgatggatgatatggtaccgagggaactgtggtcttgccttcgaaag
gggacttcatgttatggtaccacaggaccagttatcgaagcatccttgttttcaatcgca  poly-A
tctttttccccgatgcctcgagtacatgatgcccatagtgagtcgtagcacaccagcc   begins
acaccacctacctcccttcccgcaacgccatcatgcggtacgccaaatcaaggtcctcca
caatcccatgccaaatcgccgcacctccgcacagcaacctcgatcc
```

Fig. 15 (Continued)

SEQUENCE LISTING

<160> NUMBER OF SEQ ID NOS: 8

<210> SEQ ID NO 1
<211> LENGTH: 3116
<212> TYPE: DNA
<213> ORGANISM: Melanocarpus albomyces

<400> SEQUENCE: 1

```
gaattcagga tggcatcgag tgaagggcga ggaggatgtg ccgaatacga gctcgtcgac      60
ggcttcctgc tccgtcctgc gctctcctgg gatcgagcgg catggggatt tcttctatat     120
aaggggctcg acagtcgcga tcatgagatt gattttcca ccctcaccag gcacaagcca      180
gccatcagaa cctctcttcc accttcatca ggcactctcc ttccgtctgt cgagctcttt     240
cccacatttc tagcaggcgg tttcgacacc agccgtcttc acaccatgaa gaccttcacc     300
agcgccctgg cgctcgtggt gggcatgctt gccccgggtg ccgtcgttgc cgcgcctccc     360
agcactccgg cccagcgaga tctggtcgag ctgcgcgagg cgaggcagga gggcggcaag     420
gacctccgtc cccgtgagcc gacgtgcaac acgccgagca accgggcgtg ctggagcgac     480
ggcttcgaca tcaacaccga ctacgaagtc agcacgccgg ataccggcgt cactcagtct     540
gtgagtcctc ctctccgccc ccttggtttc gggaaggctg tccgaaggga aggaaagtcc     600
gaggctaact gcagacagta cgtattcaac ctcactgagg ttgacaactg gatgggccca     660
gacggcgtcg tcaaggagaa ggtgatgttg atcaatggtg agtcgaccgc gaatgggatg     720
tcgagttgcc atccaaaata gacctgtgta actgactggt tcgatcacag ggaacattat     780
gggtacgtct tatctggctg tcccggcacg ccaatggcct ttcttttcct tgagcgtagg     840
acgtgcgacg gactgactga gaacaatagg ccccaacatc gtcgcgaact ggggtgatac     900
ggtcgaggtc accgtgatca acaaccttgt gaccaacgga acgtcgatcc actggcacgg     960
catccaccag aaggacacca acctgcacga cggcgccaac ggcgtgaccg agtgtccgat    1020
cccgcccaag gcggccagc ggacgtaccg ctggcgggcg cggcagtatg caccagctg      1080
gtaccactcg cacttctcgg cgcagtacgg caacggcgtg gtgggcacga tccagatcaa    1140
cggcccggcg tcgctgccct acgacatcga ccttggcgtg ttccccatca ccgactacta    1200
ctaccgggcc gccgacgacc tggtgcactt cacgcagaac aacgcgccgc ccttcagcga    1260
caacgtgctc atcaacggca cggccgtcaa cccgaacacg ggcgagggcc agtacgccaa    1320
cgtgacgctc acgccgggca gcggcaccg cctgcgcatc tcaacacgt cgaccgagaa      1380
ccacttccag gtgtcgctcg tcaaccacac catgacggtc atcgccgccg acatggtgcc    1440
cgtcaacgcc atgacggtcg acagcctgtt cctggccgtc ggccagcgct acgacgtcgt    1500
catcgacgcc tcgagagccc cggacaacta ctggttcaac gtcacctttg gcggccaggc    1560
ggcgtgcggc ggctcgctca acccgcaccc ggccgccatc ttccactacg ccggcgcgcc    1620
cggcggcctg cccaccgacg agggcacgcc cccggtcgac caccagtgcc tggacacgct    1680
cgacgtgcgc cccgtcgtgc cgcgcagcgt gcccgtcaac agcttcgtca gcggcccga    1740
caacacgctg ccggtggcgc tcgacctgac cggcacgccc ctgttcgtgt ggaaggtcaa    1800
cggcagcgac atcaacgtcg actggggcaa gccatcatc gactacatcc tcaccggcaa     1860
caccagctac cccgtgtcgg acaacatcgt gcaggttgat gccgtcgatc aggtatgtcc    1920
tctgttaaag cctacgtcg tacgattgcg ctggcaaatc acacctcgta ctgacgccaa     1980
accaccacct cccttctagt ggacatactg gctcatcgag aacgatccgg agggccctt     2040
```

-continued

```
cagcctgccg cacccgatgc acctccacgt aagtggccaa ccctgtcacg tacgttgcaa    2100
ccgccctctc ccgggccccc caactcacac ttcggactcc cgtcccacag ggccacgact    2160
tcctcgtgct ggggcggtcg cccgacgtgc cggcggcgtc gcagcagcgc ttcgtgttcg    2220
acccggccgt ggacctggcg cggctcaacg gcgacaaccc gccgcggcgc gacaccacga    2280
tgctgccggc cggcggctgg ctgctgctcg ccttccgcac cgacaacccg ggcgcctggc    2340
tcttccactg ccacatcgcc tggcacgtgt cgggcggcct gtcggtcgac ttcctcgagc    2400
gccccgccga cctgcgccag cgcatctccc aggaggacga ggacgacttc aaccgcgtct    2460
gcgacgagtg gcgcgcctac tggccgacga atccctaccc caagatcgac tcgggcctga    2520
agcgtcgccg ctgggtggag gagagcgagt ggctggttcg ttgatggggg aaaggggggg    2580
taggtgcgat tcagggtac ctagggtgca cttgatgttg atgctcgatg gagaattggt    2640
tttggttact tgttgttcac tttcgacatg cgttggtcct tgtttggatt ttttaggttg    2700
tccagatgat ggatgatatg gtaccgaggg aactgtggtc ttgccttcga aagggggactt    2760 catgttatgg taccacagga ccagttatcg aagcatcctt gttttcaatc gcatcttttt    2820
tcccccgatg cctcgagtac atgatgccca tagtgagtcg tagcacacca gccacaccac    2880
ctacctccct tcccgcaacg ccatcatgcg gtacgccaaa tcaaggtcct ccacaatccc    2940
atgccaatcg ccgcacctcc gcacagcaac ctcgatcctc ctccggaacg cctcgccagc    3000
atcaatcgcc cgcccaaccc cccgtacatc accaccaggc gaaggctccg tctcgtccac    3060
cccaaccacc cgccagtacc gcagcagccc gacgtcctct cgaccggcgc aagcac        3116
```

<210> SEQ ID NO 2
<211> LENGTH: 623
<212> TYPE: PRT
<213> ORGANISM: Melanocarpus albomyces

<400> SEQUENCE: 2

Met Lys Thr Phe Thr Ser Ala Leu Ala Leu Val Val Gly Met Leu Ala
1               5                   10                  15

Pro Gly Ala Val Ala Ala Pro Pro Ser Thr Pro Ala Gln Arg Asp
            20                  25                  30

Leu Val Glu Leu Arg Glu Ala Arg Gln Glu Gly Gly Lys Asp Leu Arg
        35                  40                  45

Pro Arg Glu Pro Thr Cys Asn Thr Pro Ser Asn Arg Ala Cys Trp Ser
    50                  55                  60

Asp Gly Phe Asp Ile Asn Thr Asp Tyr Glu Val Ser Thr Pro Asp Thr
65                  70                  75                  80

Gly Val Thr Gln Ser Tyr Val Phe Asn Leu Thr Glu Val Asp Asn Trp
                85                  90                  95

Met Gly Pro Asp Gly Val Val Lys Glu Lys Val Met Leu Ile Asn Gly
            100                 105                 110

Asn Ile Met Gly Pro Asn Ile Val Ala Asn Trp Gly Asp Thr Val Glu
        115                 120                 125

Val Thr Val Ile Asn Asn Leu Val Thr Asn Gly Thr Ser Ile His Trp
    130                 135                 140

His Gly Ile His Gln Lys Asp Thr Asn Leu His Asp Gly Ala Asn Gly
145                 150                 155                 160

Val Thr Glu Cys Pro Ile Pro Pro Lys Gly Gly Gln Arg Thr Tyr Arg
                165                 170                 175

Trp Arg Ala Arg Gln Tyr Gly Thr Ser Trp Tyr His Ser His Phe Ser

-continued

```
            180                 185                 190
Ala Gln Tyr Gly Asn Gly Val Val Gly Thr Ile Gln Ile Asn Gly Pro
            195                 200                 205
Ala Ser Leu Pro Tyr Asp Ile Asp Leu Gly Val Phe Pro Ile Thr Asp
            210                 215                 220
Tyr Tyr Tyr Arg Ala Ala Asp Asp Leu Val His Phe Thr Gln Asn Asn
225                 230                 235                 240
Ala Pro Pro Phe Ser Asp Asn Val Leu Ile Asn Gly Thr Ala Val Asn
            245                 250                 255
Pro Asn Thr Gly Glu Gly Gln Tyr Ala Asn Val Thr Leu Thr Pro Gly
            260                 265                 270
Lys Arg His Arg Leu Arg Ile Leu Asn Thr Ser Thr Glu Asn His Phe
            275                 280                 285
Gln Val Ser Leu Val Asn His Thr Met Thr Val Ile Ala Ala Asp Met
            290                 295                 300
Val Pro Val Asn Ala Met Thr Val Asp Ser Leu Phe Leu Ala Val Gly
305                 310                 315                 320
Gln Arg Tyr Asp Val Val Ile Asp Ala Ser Arg Ala Pro Asp Asn Tyr
            325                 330                 335
Trp Phe Asn Val Thr Phe Gly Gly Gln Ala Ala Cys Gly Gly Ser Leu
            340                 345                 350
Asn Pro His Pro Ala Ala Ile Phe His Tyr Ala Gly Ala Pro Gly Gly
            355                 360                 365
Leu Pro Thr Asp Glu Gly Thr Pro Pro Val Asp His Gln Cys Leu Asp
            370                 375                 380
Thr Leu Asp Val Arg Pro Val Val Pro Arg Ser Val Pro Val Asn Ser
385                 390                 395                 400
Phe Val Lys Arg Pro Asp Asn Thr Leu Pro Val Ala Leu Asp Leu Thr
            405                 410                 415
Gly Thr Pro Leu Phe Val Trp Lys Val Asn Gly Ser Asp Ile Asn Val
            420                 425                 430
Asp Trp Gly Lys Pro Ile Ile Asp Tyr Ile Leu Thr Gly Asn Thr Ser
            435                 440                 445
Tyr Pro Val Ser Asp Asn Ile Val Gln Val Asp Ala Val Asp Gln Trp
            450                 455                 460
Thr Tyr Trp Leu Ile Glu Asn Asp Pro Glu Gly Pro Phe Ser Leu Pro
465                 470                 475                 480
His Pro Met His Leu His Gly His Asp Phe Leu Val Leu Gly Arg Ser
            485                 490                 495
Pro Asp Val Pro Ala Ala Ser Gln Gln Arg Phe Val Phe Asp Pro Ala
            500                 505                 510
Val Asp Leu Ala Arg Leu Asn Gly Asp Asn Pro Pro Arg Arg Asp Thr
            515                 520                 525
Thr Met Leu Pro Ala Gly Gly Trp Leu Leu Leu Ala Phe Arg Thr Asp
            530                 535                 540
Asn Pro Gly Ala Trp Leu Phe His Cys His Ile Ala Trp His Val Ser
545                 550                 555                 560
Gly Gly Leu Ser Val Asp Phe Leu Glu Arg Pro Ala Asp Leu Arg Gln
            565                 570                 575
Arg Ile Ser Gln Glu Asp Glu Asp Phe Asn Arg Val Cys Asp Glu
            580                 585                 590
Trp Arg Ala Tyr Trp Pro Thr Asn Pro Tyr Pro Lys Ile Asp Ser Gly
            595                 600                 605
```

Leu Lys Arg Arg Arg Trp Val Glu Glu Ser Glu Trp Leu Val Arg
    610                 615                 620

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 3
tgccacactg ccgccaaccg tgct                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 4
gttcttgata taccaatcag gatg                                          24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 5
gccggtgagg atgtagtcga tgat                                          24

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 6
aggtgacgtt gaaccagtag ttgtc                                         25

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 7
ctggtgcact tcacgcagaa caa                                           23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 8
agaaccactt ccaggtgtcg ct                                            22

LACCASE ENZYME AND THE GENE ENCODING THE ENZYME

This application is the national phase under 35 U.S.C. § 371 of PCT International Application No. PCT/FI01/00503 which has an International filing date of May 23, 2001, which designated the United States of America.

The invention relates to new laccase enzymes. The object of the invention is a new laccase enzyme, an enzyme preparation, and a gene encoding the enzyme in particular. Another object of the invention is the use of laccase in various applications.

Laccases (EC 1.10.3.2) belong to blue copper oxidases. According to a definition, laccases are p-diphenol oxidases. In addition to diphenols, laccases oxidize many other substrates, such as methoxy substituted phenols and diamines. With respect to their substrates, laccases are amazingly unspecific. Namely because of their broad substrate specificity and, on the other hand, their ability to oxidize phenolic compounds, laccases have aroused a great interest in industrial applications. Promising fields of application for laccases include, for example, delignification and the gluing of fibreboards in the forest industry, dyeing of fabrics and detoxification of dye house effluents in the textile industry, as well as use in different biosensors. With the aid of mediators, i.e., intermediary molecules, laccases also oxidize substrates that they otherwise would not be able to oxidize. The mediators are small-molecule compounds that are oxidized by laccases. The oxidized mediator, in turn, oxidizes the actual substrate.

The first laccase was found as early as 1883 in the Japanese lacquer tree (*Rhus vernicifera*). Laccases have been found in many plants, such as peach, tomato, mango, and potato; laccases have also been found in some insects. However, most known laccases originate in white rot fungi. The following genera, for example, produce laccase: *Agaricus, Aspergillus, Cerrena, Curvularia, Fusarium, Lentinius, Monocillium, Myceliophtora, Neurospora, Penicillium, Phanerochaete, Phlebia, Pleurotus, Podospora, Schizophyllum, Sporotrichum, Stagonospora* and *Trametes*. In nature, the functioning of laccases relates to the decomposition of lignocellulose, the biosynthesis of cell walls, the browning reactions of fruit and vegetables, as well as the prevention of microbial attacks on plants, among others.

Many fungal laccases have been isolated and some genes that encode them have been cloned. For example, Saloheimo et al. (1985) isolated and characterized the laccase gene of the *Phlebia radiata*, and Kojima et al. (1990) the laccase genes of the *Coriolus hirsutus* from white-rot fungus, and Berka et al. (1997), WO 95/33836, the gene of the *Myceliophtora thermophila* laccase. The natural production levels of laccases are often very low. Efforts have been made to improve production by expressing laccase genes in foreign production hosts. For example, Saloheimo and Niku-Paavola (1991; WO92/01046) successfully produced *Phlebia radiata* laccase in the fungus *Trichoderma reesei*. Laccases have also been produced heterologously, in the *Aspergillus oryzae* fungus (Yaver et al., 1996, Berka et al. 1997 and WO 95/33836), and in the *Pichia pastoris* yeast (Jönsson et al., 1997).

The expression of a laccase originating in the *Coprinus* genus in the fungus of the *Aspergillus* genus is described in the patent publication WO 97/08325. Similarly, the expression of the laccase originating in the *Polyporus pinsitus* species and the laccase originating in the *Scytalidium* genus in the fungus of the *Aspergillus* genus are described in the patent publications U.S. Pat. Nos. 5,770,418 and 5,843,745, respectively.

The temperature and pH properties of laccases isolated from various organisms differ from each other. They also depend on the substrate used. As the majority of laccases that are known function best at an acidic pH and a rather low temperature, their properties are not optimal for the applications. Some thermostable or neutral laccases have been reported but, generally, the thermostable or neutral laccases are either thermostable or neutral, not both. For example, Heinzkill et al. (1998) found laccases with an unusually high pH optimum from the fungi of the *Coprinaceae* genus. However, in 60 minutes, the activity of all the laccases that were found decreased to below 30% from the initial level at 60° C. A patent (WO96/06930) has been applied for the use of these laccases in bleaching textile dyes, but the application does not mention the activity of these laccases at high temperatures. The application examples were made at a temperature of 30–35° C. Patent application WO95/07988 describes a neutral laccase from the fungus *Rhizoctonia solani*, but the application does not study the applicability of this laccase at high temperatures in addition to alkaline conditions. On the other hand, the patent application WO98/55628 describes a thermostable laccase from the *Trametes versicolor* TV-1 strain, but according to the patent, the activity of this laccase is best at pH 2. The *Trametes versicolor* TV-1 laccase is not pH stable either; its residual activity at pH 6 after 60 minutes of incubation is about 60% of the original. Patent application WO95/33836 describes a neutral *Myceliophtora thermophila* laccase that in hair dyeing works at pH 7, but the temperature in the application example was 30° C. The publication Berka et al. (1997) reports that the *Myceliophtora thermophila* laccase retains 100% of its activity at 60° C. for 20 minutes and its optimum activity is at pH 6.5.

Patent publications JP8070861 and JP9056378 describe *Trametes* laccases, which have been reported to be thermostable and their pH optimum has been reported to be 5.0. In addition, Diamantidis et al. (2000) have characterized a bacterial laccase from the *Azospirillum lipoferum* bacterium. They reported that the laccase was thermostable for 10 min at 70° C. and the pH optimum was 6.0.

The publication Bharathi and Ramalingam (1993) describes the phenoloxidase of a clam, its maximum activity being at pH 6.8 and more than 50% of its activity remaining when incubated at 60° C. for 10 min. Patent publication EP-A1-0852260 describes polyphenoloxidases from the species of the *Myrothecium* genus, their pH optimum being 8.5–9 and the optimum temperature at 60–70° C. It is known that the fungi of the *Myrothecium* genus produce toxins.

When comparing the temperature and the pH optimum values specified for various enzymes, it should be noted that the substrate used has an effect on the values. Phenolic substrates, such as guaiacol and syringaldazine, provide higher values than non-phenolic substrates, such as ABTS.

The following patent publications suggest the use of laccases in wood-processing applications: WO 9954545, U.S. Pat. No. 5,691,193, DE 4137761, EP 408803 and WO 9523232.

The purpose of this invention is to eliminate the disadvantages related to prior art and to provide quite a new kind of enzyme preparation containing laccase activity. Especially, the enzyme preparation can be used in applications, which need to tolerate both high temperatures and a high pH. There are such applications, for example, in the wood-processing industry and other processing industries.

The present invention introduces a new laccase that has both better temperature and pH properties, and especially the thermal stability, than the known laccases in applications that require a neutral or alkaline pH and a temperature of over 40° C.

To be more precise, the object of the invention is a laccase enzyme specified in claim 1.

The laccase enzyme according to the invention can be isolated from the strains of the *Melanocarpus* genus. As far as we know, no laccase isolated from the strains of the *Melanocarpus* genus has been described earlier. The laccase according to the invention can preferably be isolated from the strains of the *M. albomyces* species, especially from the IMI 255989 strain, samples of which are freely available from the CABI Bioscience UK centre CABI GRC strain collection (Egham) (Bakeham Lane Egham Surrey DW20 9Ty, UK). The strain was deposited in the collection in 1981. In 1996, the strain was also deposited in the Culture Collection of VTT Biotechnology (Technical Research Centre of Finland VTT, at the address: VTT Biotekniikka, PL1500, 02044 VTT, Espoo, Finland) and given the number VTT-D-96490. Samples of this deposition are also freely available. This strain is described in the publication Ravanko (1996), which studied the laccase activity of the culture solution of the strain at various temperatures and pH values. However, the publication does not describe the isolation and the purification of the laccase.

The laccase enzyme according to the invention works over the range of pH 3–9, preferably 4–8, more preferably 5–8, even more preferably 6–8, most preferably 6.5–7.5. The laccase activity is at its highest over the range of pH 7–8, the highest at about 7.5. Thus, the pH optimum of the enzyme is quite wide and ranges over pH 5–7.5; preferably the pH optimum is 7.5. The activity of the enzyme is at its highest within 30–80° C., preferably within 40–80° C., more preferably within 50–80° C., even more preferably within 60–80° C., most preferably within 60–70° C. The best activity of the enzyme occurs at a temperature of about 70° C.

The laccase according to the invention retains well its activity at high temperatures. In the conditions described in Example 3, more than 50% of the activity of the laccase of the culture solution remains after incubating at 60° C. for 1 hour. After incubating at 70° C. for 15 min, about 30% of the activity of the enzyme remains, and after incubating at 70° C. for 30 min, about 10%. At 80° C., the enzyme withstands incubation for about 5 min in the conditions described in Example 3. In some applications, e.g., in the forest industry, even a tolerance for a short time at high temperatures provides considerable advantages. When further studying the activity of the pure enzyme, it was discovered that the thermal stability of the enzyme was exceptionally good and clearly better than that of the laccases previously described. At 60° C., the enzyme retained its activity essentially unchanged for 2 hours, as indicated by Example 3 and FIG. 7. The thermal stability of the *Myceliophtora* laccase characterized by Berka et al. (1997) remained at 60° C. for 20 min only.

Furthermore, the pH stability of the laccase enzyme according to the invention improves, when the pH increases. After 22-hour incubation at pH 4, the residual activity is 65%, the residual activity in the same conditions at pH 5 is about 80%, the residual activity at pH 6 is about 85%, the residual activity at pH 7 is about 90%, and at pH 8 as much as over 90%, about 92%. Together with the pH optimum, this property makes it advantageous to use the enzyme according to the invention at high pH values.

The isoelectric point of the laccase according to the invention is about 4.0 when measured by isoelectric focusing, whereby the accuracy of the definition is about ±0.5.

When determined by SDS-PAGE, the molecular weight of the laccase according to the invention is about 80 kDa. The accuracy of the SDS-PAGE definition is in the order of +/−5 kDa.

The objective of the invention is a laccase in particular, which, when purified, has an isoelectric point of about 4.0 as measured by isoelectric focusing, and a molecular weight of about 80 kDa. The pH optimum of the laccase is about 7.5 and the temperature optimum about 70° C. when measured with a purified enzyme. The laccase can be isolated from the strains of the *Melanocarpus* genus, preferably from the strains of the *Melanocarpus albomyces* genus, most preferably from the *M. albomyces* IMI 25598 strain. Another objective of the invention is an isolated and purified laccase enzyme.

A further object of the invention is an enzyme preparation containing the laccase enzyme according to the invention. The amount of laccase enzyme in the enzyme preparation is preferably higher than that of the strains of the *Melanocarpus* genus, especially the strains of the *Melanocarpus albomyces* species, especially the amount of enzyme naturally produced by the *M. albomyces* IMI 255989 strain in its culture solution in growth conditions, which are not optimised to produce laccase. The amount of laccase in the enzyme preparation is preferably over 10 mg/l, more preferably ≧30 mg/l, even more preferably ≧300 mg/l, still even more preferably ≧500 mg/l; most preferably ≧1 g/l.

As stated above, the laccase according to the invention can be isolated from the strains of the *Melanocarpus* genus, especially from the strains of the *Melanocarpus albomyces* species, especially from the *M. albomyces* IMI 255989 strain, but it can also be produced by the recombination technique by isolating genes that encode the laccases according to the invention and transferring them into a suitable production host.

The laccase according to the invention can be produced in the culture solution of its natural host or a production host, from where it can be isolated and purified by using known methods of protein chemistry. If the culture solution contains a high enough amount of laccase, but no other detrimental proteins, the culture solution may be used as such by simply separating the cells. The culture solution can possibly be concentrated. In different applications, it is preferable to use an enzyme preparation containing an increased amount of laccase. The increased amount of laccase can be prepared by producing the laccase enzyme in the culture solution of the production host by means of recombinant technology. The increased amount refers to an amount of laccase enzyme, which exceeds the amount of laccase enzyme naturally produced by the strains of the *Melanocarpus* genus, especially the *M. albomyces* strain, especially the IMI 255989 strain.

A further object of the invention is an enzyme preparation containing an essential amount of the laccase enzyme according to the invention. This means that the laccase is the main activity of the enzyme preparation without any considerable amounts of other enzymes. A further object of the invention is also an enzyme preparation containing a laccase that can be isolated from the fungus of the *Melanocarpus* genus, and additives that are needed for the respective application. Such additives can comprise, for example, buffers and stabilizers.

An object of the invention is also a nucleic acid molecule that encodes laccase. The nucleic acid molecule is selected from the group comprising:
- a nucleic acid molecule comprising the coding region of the nucleotide sequence as depicted in SEQ ID NO:1 or FIG. 15;
- a nucleic acid molecule that encodes a polypeptide that comprises the amino acid sequence as depicted in SEQ ID NO:2 or FIG. 15;
- a nucleic acid molecule comprising a coding sequence that differs from the coding sequence of the nucleotide sequence of SEQ ID NO:1 or FIG. 15 due to the degeneracy of the genetic code;
- a nucleic acid molecule that hybridizes to the nucleotide sequence of SEQ ID NO:1 or FIG. 15; and
- a nucleic acid molecule that encodes a polypeptide, which has laccase activity and the amino acid sequence of which shows at least 73% identity with the amino acid sequence of SEQ ID NO:2 or FIG. 15.

The invention also embodies nucleic acid molecules that encode polypeptides, the amino acid sequence of which shows at least 75% identity with SEQ ID NO:2 or the amino acid sequence of FIG. 15, preferably at least 80% identity, more preferably at least 85% identity, even more preferably at least 90% identity; most preferably at least 95% identity. It is most preferable if the amino acid sequence of the polypeptides according to the invention shows at least 99% identity with ID NO:2 or the amino acid sequence of FIG. 15. If the similarity is assessed on the basis of homologous amino acids, the invention embodies the nucleic acid molecules, which encode polypeptides, the amino acid sequence of which is at least 83% homologous to SEQ ID NO:2 or the amino acid sequence of FIG. 15, preferably at least 85% homologous, more preferably at least 90% homologous, even more preferably at least 95%, most preferably at least 99% homologous to SEQ ID NO:2 or the amino acid sequence of FIG. 15.

The invention also embodies the nucleic acid molecules, which are hybridised to the sequence SEQ ID NO:1 in hybridising conditions, where the hybridisation solution contains 6×SSC, 5×Denhadt's reagent, 0.5% SDS, 100 µg/ml denatured DNA and hybridisation is carried out at 50–60° C. Another alternative is that the hybridisation solution contains 6×SSC, 5×Denhadt's reagent, 0.5% SDS, 100 µg/ml denatured DNA, 50% formamide and, in that case, hybridisation is carried out at 25–35° C. The invention especially embodies those nucleic acid molecules, which are hybridised to the SEQ ID NO:1 sequence in stringent conditions, whereby hybridisation is carried out in accordance with the first alternative, otherwise in the same conditions, but at 68° C. and, according to the second alternative, at 42° C. 50×Denhadt is 10 g/l Ficoll, 10 g/l polyvinyl pyrrolidone, 10 g/l bovine serum albumin and the SSC is 0.15 M NaCl, 0.015 M sodium citrate, pH 7.0.

The nucleic acid molecules refer to DNA, RNA or, for example, cDNA.

The invention also relates to polypeptides, which have laccase activity and which are encoded by the nucleic acid molecules defined above. The invention further relates to polypeptides, the amino acid sequence of which, in the way described above, is identical or homologous with SEQ ID NO:2 or the amino acid sequence of FIG. 15.

The invention also relates to a method for producing laccase, comprising the following steps:
- a nucleic acid molecule or vector according to the invention is transferred into a micro-organism host cell to express the nucleic acid molecule and, optionally, to secrete it from the host cell; and
- a polypeptide that has laccase activity is recovered either from the cells or the culture solution of the micro-organism host.

The laccase according to the invention is exceptionally well suited to industrial applications, wherein the prevailing pH and temperature conditions are high. Such applications include those of the forest industry, which affect lignin or extractives (either directly or by mediators), manufacture of fibre products and boards from mechanically ground lignin-containing fibres, improvement of the runnability of paper machines, and other applications, oxidation of polymers, such as lignin, cellulose, and/or starch (either directly or by mediators), as well as oxidation of other chemicals, such as alkenes or colour molecules. In these applications, the temperature is often over 60° C., generally as high as 80° C., and the pH is close to neutral or slightly higher. The enzyme according to the invention works extremely well in conditions, where both the pH and the temperature are simultaneously rather high.

In the following, the invention is described in detail with the aid of the appended figures and examples.

FIG. 15 shows a gene that encodes the *Melanocarpus albomyces* laccase (residues 286–2978 of SEQ ID NO: 1), and a corresponding amino acid sequence (SEQ ID NO: 2)

Figure 1:
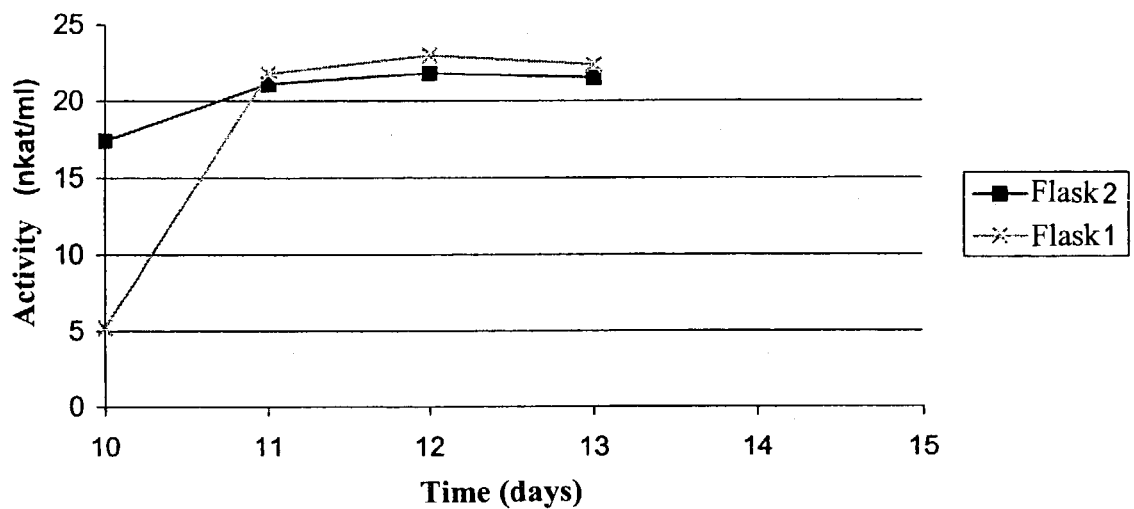
FIG. 1 shows the production of the *M. albomyces* laccase in shake flask cultivation.

The term "enzyme preparation" used in this application refers to any product that contains laccase enzyme activity. The enzyme preparation can be, for example, a culture solution containing laccase, an isolated laccase or an enzyme mixture, at least one component of which is a laccase. The enzyme preparation can also contain various additives, such as stabilizers or buffers. They are selected so as to be suitable for the respective application of the laccase enzyme preparation. The enzyme preparation can also contain other enzyme activities, such as peroxidase activity, depending on the application of the enzyme preparation.

The enzyme preparation containing laccase can also contain a suitable mediator, which is used to enhance the operation of the laccase. Suitable mediators include, e.g., Tempo (=2,2,6,6-tetramethyl-1-piperidinyloxy), HBT (=1-hydroxybenzotriazole), ABTS=2,2'-azinobis-3-ethylbenz-thiazole-6-sulphonate, violuric acid, NHA (=N-hydroxy-acetanilide).

Screening of Microbes that Produce Laccase

Microbes that produce laccase can be isolated from nature or they can be screened from already isolated and identified strains of culture collections by using screening methods that are well known in microbiology. As laccases belong to phenoloxidases, methods that are suitable for screening phenoloxidases are used in the screenings. Screenings can be carried out studying the production of the enzyme either on a solid culture on plate cultivations or in a liquid culture medium by measuring the enzyme activity.

When looking for new laccases that tolerate higher temperatures and pHs than the majority of known laccases, it is worthwhile to screen microbes from environments, where they live in warm and/or alkaline conditions. Such environments are found, for example, in composts, piles of wood chips or tropical areas.

The production of phenoloxidases by the positive fungi found in the screening can be studied on plates by adding substrates of phenoloxidases on top of the mycelium. By using these drop tests, it can be find out, whether the positive reactions on the plates are caused by peroxidases or laccases. Suitable reagents include ABTS, syringaldazine, and guaiacol, and in observing peroxidases, hydrogen peroxide.

The micro-organism, which produces phenoloxidase and which is found as a result of screening is cultivated on a suitable medium, and the formation of phenoloxidase in the culture solution is observed by a method that is suitable for measuring the phenoloxidase activity. Suitable culture media for fungi include, for example, malt extract and potato dextrose media, and suitable substrates for measuring the activity include ABTS, guaiacol, and syringaldazine. For many fungi, the production of phenoloxidases requires an inducer. These include, for example, aromatic compounds, materials containing lignin, surface-active agents, certain sources of carbon, and copper sulphate. The laccase activity can be measured by using ABTS as a substrate, the laccase oxidizes it dark green. The measurement can be made in accordance with the method of Niku-Paavola et al. (1988). The laccase activity can also be measured by using a guaiacol method in accordance with the method of Paszczynski et al. (1985).

After a sufficient amount of an interesting laccase has been produced, the enzyme is purified and its properties are characterised. The temperature and pH behaviour as well as the isoelectric point of the enzyme can be determined.

Laccase producers can also be screened by the homology of the sequences of the laccase genes. In that case, nucleotides based on the conserved regions of the amino end of the laccase genes can be used as primers in PCR, and look for gene sequences, which are homologous to known laccases, in the genome of various fungi, for example.

Determination of laccase activity at various temperatures can be carried out by the ABTS method, as described in Example 1. The pH optimum of the laccase can be determined by the guaiacol method in a suitable buffer at different pH values. When the pH is over 7, the operation of the ABTS in the activity analysis weakens.

The thermal stability can be determined by incubating an enzyme sample at various temperatures in a suitable buffer at a certain pH. The residual activity of the enzyme at each temperature can be defined by the ABTS method, for example.

The pH stability can be determined by incubating the enzyme sample at various pH values in a suitable buffer. The residual activity can be determined by the ABTS method, for example.

Isolation and Purification of Laccase

The enzyme can be purified by using conventional methods of enzyme chemistry, such as salt precipitation, ultrafiltration, ion exchange chromatography, and hydrophobic interaction chromatography. Purification can be monitored by SDS polyacrylamide gel electrophoresis. The enzyme activity of the purified enzyme at various temperatures and pH values can be determined; similarly, the molecular weight and the isoelectric point can be determined.

In the examples of this invention, the production of laccase is described by cultivating the *Melanocarpus albomyces* strain on a rich culture medium. During cultivation, the laccase activity was monitored in accordance with the ABTS method of Niku-Paavola et al. (1988), based on the generation of a dark green cation radical from the ABTS under the effect of the laccase. However, the invention is not limited to the *M. albomyces* laccases produced on this medium only.

The *M. albomyces* laccase was purified from a culture solution, from which the cells were removed by filtration or centrifugation. The culture solution was further concentrated using ultrafiltration. An anion exchange chromatography, and hydrophobic interaction chromatography were used for further purification. The molecular weight cut off value in ultrafiltration was about 30 kDa. The anion exchange chromatography was carried out at pH 5 in an acetate buffer, and the laccase was eluted from the column with an increasing linear gradient of $Na_2SO_4$. The best fractions of the ion exchange were further purified by hydrophobic interaction chromatography, at pH 5 in an acetate buffer. The sample was bound at 0.7 M $Na_2SO_4$ concentration and eluted with a decreasing linear gradient of $Na_2SO_4$.

However, it is possible to separate the enzyme by using other known purification methods as well.

The molecular size, the isoelectric point, and the pH and temperature profiles of the purified *M. albomyces* laccase were determined.

The purified enzyme refers to an enzyme preparation, which has no other proteins in addition to the laccase band, which can be observed, as defined by SDS-PAGE and Coomassie staining. In this application, the enzyme is purified by ultrafiltration, anion exchange chromatography, and hydrophobic interaction chromatography. The purity of the obtained laccase that is essentially free from other proteins is $\geq 90\%$.

The molecular size of the purified *M. albomyces* laccase was 80 kDa, determined by SDS polyacrylamide gel electrophoresis. In isoelectric focusing by the Multiphor II electrophoresis equipment (Pharmacia LKB), 4.0 was determined as the isoelectric point. The activity of the *M. albomyces* laccase was highest at the temperature of 70° C. and its pH optimum was 7.5. After 2 hours of incubation at 60° C., the *M. albomyces* laccase retained 100% of its activity. Furthermore, its pH stability improved, when the pH increased.

Production of Laccase

The laccase according to the invention can be produced in the culture solution of its natural host or a production host, from where it can be isolated and purified by using known methods of protein chemistry. If the culture solution contains a sufficiently high amount of laccase but no other detrimental proteins, it may be possible to use the culture solution as such by simply separating the cells. When so desired, the culture solution can be concentrated and/or purified. It is preferable to use, in various applications, an enzyme preparation containing an increased amount of laccase. Such an enzyme preparation can be prepared by producing the increased amount of laccase enzyme in the culture solution of the production host by means of gene technology. The increased amount refers to an amount of laccase enzyme, which exceeds the amount of laccase enzyme naturally produced by the *M. albomyces* strain, strain IMI 255989 in particular.

The laccase according to the invention can also be produced by recombinant technique by isolating the genes that encode the laccases according to the invention and by transferring them to a suitable production host. The laccase-encoding genes can be isolated from a cDNA library in any of the following ways. The cDNA library can be built in a suitable yeast expression vector and transformed into *Saccharomyces cerevisiae* yeast, for example. The clones that produce laccase are identified, for example, on the basis of activity by using plates that contain ABTS substrate. Another possibility is to connect the cDNA library to a λZAP vector and infect the *Escherichia coli* cells with the obtained production bank. The clones that encode laccase are identified either with the aid of a polyclonal antibody or DNA hybridisation. If polyclonal antibodies are used, they are produced against a purified laccase protein in a rabbit, for example. In hybridisation, fragments of the laccase gene provided by PCR are used as a probe. In that case, the sequences of the PCR primers are either based on the regions generally conserved in the laccase genes (e.g., regions that correspond to the amino acids of the active centre) and/or on the sequence of the amino-terminal end of the purified laccase protein or that of an internal peptide. Furthermore, the oligodT region bound to the polyA region of the tail of each messenger RNA can be used as the PCR primer.

The isolated laccase cDNAs are sequenced. The connection between the isolated cDNA and the isolated enzyme can be ascertained by amino acid sequencing, which is made of the enzyme. The chromosomal copy of the laccase gene can either be isolated by PCR or from the genomic library made in the λ vector, and the locations of the introns can be established by sequencing.

Isolation of the Gene of the *M. albomyces* Laccase

It was not possible to isolate the gene of the *M. albomyces* laccase on the basis of the messenger RNA and the cDNA library. Creating a representative cDNA library was not successful. Surprisingly, a problem was caused by the fact that *M. albomyces* produces laccase in the late cultivation phase, when many cells were already autolyzed, and the messenger RNA partially degradad or it is difficult to isolate pure. Therefore, instead of the cDNA library, the gene had to be isolated from a genomic gene library. The isolation of the gene is described in detail in Example 9.

The sequence of the laccase gene is shown in FIG. 15 and in the sequence listing (SEQ ID NO:1). The length of the gene is 2279 bp, including introns. As FIG. 15 shows, the number of the base that starts the encoding region is 286, the introns are in positions 541–618, 698–770, 783–869, 1913–1999, 2069–2150. The last encoding base is 2561.

The gene encodes a polypeptide of a length of 623 amino acids. When comparing the amino acid sequence, by using the Blast method (Altschul et al., 1990), with the amino acid sequence of *Myceliophtora* disclosed in patent application WO 9533836, it was discovered that the amino acid sequences were 72% identical (identities 450/623, 72%) and 82% homologous (positives 518/623, 82%; positives refer to homologous amino acids), (gaps=4/623, 0%).

When a corresponding comparison was made with *Podospora anserina* laccase (Fernandez-Larrea and Stahl, 1996), it was discovered that the sequences were 68% identical (identities 427/627, 68%), and 79% homologous (positives 502/627, 79%) (gaps=12/627, 1%).

The isolated laccase gene is utilized in protein production in other organisms. Such production hosts include the *Aspergillus* production systems mentioned above, such as *A. oryzae* or *A. niger* (U.S. Pat. Nos. 5,843,745, 5,770,418, WO 9708325 and WO 9533386), the production system developed for the fungus *Trichoderma* (EP 244 234), or the production system developed for fungal species of *Fusarium*, such as *F. oxysporum* (Malardier et al., 1989), the production systems developed for a *Bacillus* bacterium, such as the *B. subtilis* or the *E. coli* bacterium, the yeasts *Saccharomyces*, *Shizosaccharomyces* or *Pichia pastoris*, or a *Streptomyces* actinomycete or some other microbe or mammalian cell.

Optimizing the Production of Laccase

The production of laccase can also be improved by optimising the culture conditions and the culture medium of a wild or a recombinant strain. When optimising the culture medium, for example, the effect of the quality (among others, an organic or inorganic source of nitrogen) and the quantity of the source of nitrogen on the laccase production. When needed, the source of nitrogen is limited in order to achieve a higher yield. Similarly, the effect of the source of carbon is established. A source of carbon that is optimal for the enzyme production is selected. When needed, the amount of carbon source can also be limited. The carbon/nitrogen ratio is optimised to be the best for the production of enzyme. The growing conditions are optimised to be the best possible for the enzyme production in question. The microbe is grown at a pH and temperature optimal for enzyme production. Proper mixing and air supply guarantee an optimal aeration during fermentation. In fermentation, inducers of laccase production, such as veratryl alcohol, xylidine, or lignin can also be used. The way and the time of adding the inducers, as well as their concentration are optimised.

Use of Laccase in Various Applications

Generally, the laccase according to the invention is well suited to be used in applications, wherein laccases can be used, such as gel formation, gluing of fibres, treatment of cork, removal of dye (especially textile dyes), dyeing of fibres, protein treatment, detergents, anti-microbial applications, starch applications, oxidation of chemicals, removal of biofilm, preparation of lignin derivatives, medical analysis, reducing the shrinkage of wool, baking, improving the preservability of beer, production of dye, removal of oxygen from oil products, and the production of iodine. When so desired, the laccase according to the invention can also be immobilized for certain purposes.

The laccase according to the invention is especially well suited to industrial applications, wherein the prevailing pH and temperature conditions are high. Such applications include, among others, applications of the forest industry, manufacture of fibre products and boards from mechanically ground, lignin-containing fibres, improvement of the runnability of paper machines and other applications, oxidation of polymers and that of other chemicals, such as dye molecules. In these applications, the temperature is often over 60° C., generally as much as 80° C., and the pH near neutral or slightly alkalic.

In all applications, it is essential that enough oxygen is brought to the reaction. Oxygen is the reducing substrate needed by the laccase. In some cases, especially when the substrate concentration is low, there can be enough oxygen in the reaction mixture as such but it can also be added either by bringing air or oxygen or air enriched with oxygen to the reaction mixture.

When needed, mediators are used as additives in the reactions.

The laccase according to the invention is well suited to oxidation of colouring agents, for example. The dye molecules are brought into contact with the laccase at pH 4–8, for example, at pH 4.5–7.5, preferably at pH 6–8, more preferably at pH 7–8, the temperature being within a range of 25–80° C., preferably 40–80° C., more preferably 50–80° C.; most preferably 60–80° C. Oxygen is added into the reaction as needed. The amount of laccase is 1–1000 nkat/g, preferably 10–500 nkat/g, most preferably 20–200 nkat/g of colouring agent. The reaction is allowed to take place for 5 min to 24 hours, preferably for 30 min to 2 hours.

The laccase according to the invention is also well suited to polymerisation. The selected compound to be polymerised is brought into contact with the laccase in the same conditions as described above. The reaction mixture can be aerated during the test. Polymerisation can be monitored by following the increase in the molecular weight of the polymerised compound, for example by GPC (gel permeation chromatography).

The laccase according to the invention can also be used to improve the runnability of paper machines. The laccase can be used to improve the runnability of paper machines by polymerising compounds originating from lignin and extractives and by decreasing the detrimental growth of microbes in the paper machine. Generally, the conditions in the paper machine are about pH 5–7 and the temperature 60–80° C. The laccase can be added into the process water or into the head box or the circulation water system of the paper machine without essentially needing to change the conditions prevailing at the paper machine. The pH can be within 5–8 and the temperature within 50–80° C. The amount of laccase can be 1–1000 nkat/g, preferably 10–500 nkat/g of dry matter, fibres or litres of circulation water. The treatment time can be 5 min to 24 hours, preferably 30 min to 2 hours.

The laccase according to the invention can also be used in oxidation of fibres. Lignin-containing fibres can be brought into contact with the laccase at a temperature of 50–80° C., even as high as 50–100° C., preferably at a temperature of 60–80° C., at pH 5–8, preferably at pH 6–8, the laccase concentration being 1–1000 nkat/g of fibres, preferably 10–500 nkat/g of fibres, the reaction time being 2 min to 24 hours, preferably 10 min to 2 hours. Due to the laccase treatment, the strength properties of the fibres improve, which can be utilised, for example, in the manufacture of fibre boards, such as MDF boards, or in paper or cardboard products, which are made of mechanically ground lignin-containing fibres.

In addition to the application examples mentioned above, the laccase according to the invention can also be used in delignification of fibres. The laccase can be in contact with the fibres that are to be delignified, such as kraft fibres, with the kappa value being 20–30, preferably about 25, the consistency being 5–15, preferably about 10%, preferably in the presence of a mediator the amount of mediator being 1–5% of the pulp, preferably 3% of the pulp, the pH being within 5–8, preferably within 6–8, the temperature being within 50–80° C., preferably within 60–80° C. The reaction time can be between 5 min to 24 hours, preferably 30 min to 2 hours. The amount of laccase can be 10–1000 nkat/g, preferably 10–500 nkat/g in an oxygen pressure of 0.5 Mpa.

The following examples are intended for illustration of the present invention and should not be interpreted as limiting the present invention in any way.

EXAMPLE 1

Production of *M. albomyces* Laccase

*M. albomyces* fungus was kept on oat-agar plates (Difco).

Both the inoculum and the production medium contained
25 g/l glucose (AnalaR)
27.5 g/l Bacto yeast extract (Difco)
0.5 mg/ml Indulin AT (Sigma)
0.04 l/l mineral solution containing:
    1.0 g/l $CaCl_2.2H_2O$ (Riedel-de Haën)
    1.0 g/l $FeSO_4.7H_2O$ (Riedel-de Haën)
    0.1 g/l $ZnSO_4.7H_2O$ (Merck)
    0.16 g/l $CuSO_4.5H_2O$ (Merck)
    1.0 g/l $Na_2EDTA$ (Riedel-de Haën).
The glucose solution was sterilized separately.

First, 100 ml of medium was inoculated with 3–4 pieces (about á 1 $cm^2$) cut from well grown mycelium on oatmeal agar. The cultivation temperature was 37° C. and the agitation speed 120 rpm. After 2 days of cultivation, the mycelium was homogenized, and 900 ml of the sterile culture was inoculated with 100 ml of the homogenized inoculum. The volume of the production culture was 1 l; the cultivation temperature was 37° C., and the agitation speed 160 rpm. Cultivation was continued for 14 days. Four parallel cultures were made.

Enzyme Activity Assay

The laccase activity of the *M. albomyces* culture solutions was measured by using ABTS Laccase oxidizes ABTS to a dark green cation radical. The activity assay was carried out in accordance with the method developed by Niku-Paavola et al. (1988). The sample was diluted with 0.025 M succinate buffer, pH 4.5. 0.350 ml of ABTS solution (11 g/l) was added into 1.15 ml of the dilution, and the reaction was followed for 2 minutes by the Perkin Elmer Lambda 20 spectrophotometer at a wavelength of 436 nm.

The measured laccase activities of the *M. albomyces* cultures are shown in FIG. 1.

EXAMPLE 2

Purification of *M. albomyces* Laccase

Determination of of the Protein Content

The protein contents were determined by the DC Protein Assay kit of Bio-Rad, based on a method developed by Lowry et al. (1951). The assays were carried out using the reagents of the kit, and the intensity of the colour reaction thus formed was measured on a wavelength of 750 nm by the Hitachi U-2000 spectrophotometer. Each time of measurement, a standard curve was also defined using solutions containing 0.25–1.25 g/l of bovine serum albumin (BSA, Bio-Rad).

Purification

The culture solution, from which cells had been removed by filtration, was ultrafiltrated by the Amicon 8400 filtering equipment, using a PM30 membrane (Millipore). In the filtration, the solution was concentrated and distilled water was added so that it was possible to reduce the conductivity of the solution to the level required by ion exchange chromatography. The conductivity was measured by using an EDV Instruments conductivity instrument (platinum electrode Mettler Toledo).

Figure 2:
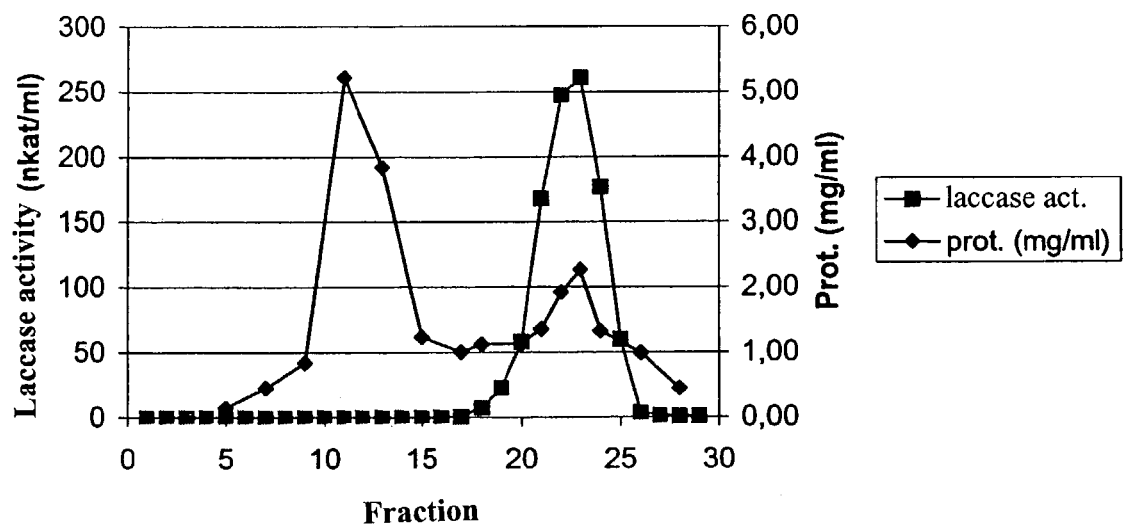
FIG. 2 shows the laccase activity and the protein content of various fractions in anion exchange chromatography.

After ultrafiltration, the solution was purified by anion exchange chromatography (DEAE Sepharose Fast Flow, h=10 cm, V=20 ml, Pharmacia). The resin was equilibrated at room temperature with 0.01 M acetate buffer, pH 5. The proteins were eluted with an increasing linear saline gradient by using 0–0.5 M sodium sulphate (Merck). The total volume of the gradient was 90 ml and the flow rate 2 ml/min. During the gradient, 4-ml fractions were collected. The protein content, laccase activity, and the conductivity of the fractions were assayed. The laccase activity and the protein content of the fractions are shown in FIG. 2.

Figure 3:
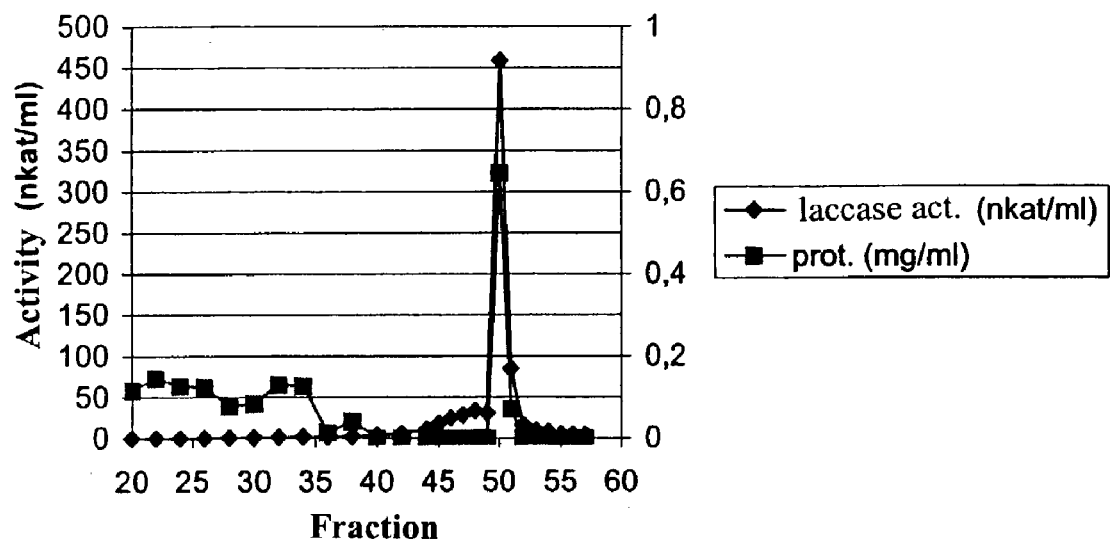
FIG. 3 shows the laccase activity and the protein content of various fractions in hydrophobic interaction chromatography.

The best laccase fractions of the anion exchange were combined, and they were further purified by hydrophobic interaction chromatography (HIC) (Phenyl Sepharose Fast Flow, h=9 cm, V=18 ml, Pharmacia). The hydrophobicity of the proteins was increased before the run by adding $Na_2SO_4$ into the sample, so that the salt content became 0.7 M. The resin was equilibrated with 1 M $Na_2SO_4$ in 0.02 M citrate buffer, pH 5, at room temperature. The sample was eluted from the column with a decreasing linear saline gradient by using 0.7–0 M $Na_2SO_4$ in citrate buffer. The total volume of the gradient was 90 ml and the flow rate 2 ml/min. After the gradient, the resin was washed with the equilibrium buffer and, finally, with water. During the gradient and subsequent washes both with buffer and water, 3.5-ml fractions were collected, the laccase activity, the protein content, and the salt content of which were measured (FIG. 3).

The most interesting fractions of both the ion exchange and HIC were analysed by SDS polyacrylamide gel electrophoresis (SDS-PAGE) for monitoring the purification of the laccase in accordance with the method of Laemmli (1970). In the gel electrophoresis, the equipment of Bio-Rad (Bio-Rad Ready Gel Cell), and ready polyacrylamide gels (12% Tris-HCl Ready Gel) were used. The gels were stained with a Coomassie Brilliant Blue R 350 dye solution (Pharmacia). The Prestained Protein Marker Broad Range #7708S (New England BioLabs) was used as the protein standard.

The molecular weight of the *M. albomyces* laccase as defined by the SDS PAGE was 80 kDa.

EXAMPLE 3

Characterization of the *M. albomyces* Laccase

Temperature Dependence of the Activity

Figure 4:
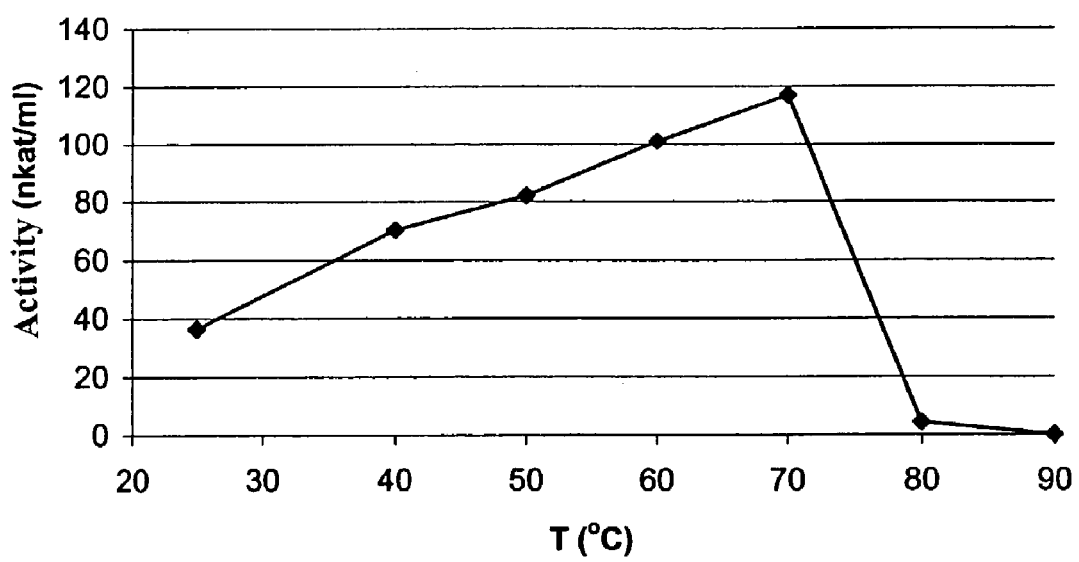
FIG. 4 shows the dependence of *M. albomyces* laccase activity on the temperature.

The dependence of activity of the purified *M. albomyces* laccase on the temperature was defined by measuring the laccase activity by ABTS at temperatures of 25, 40, 50, 60, 70, 80 and 90° C. The enzyme was diluted into tempered 0.025 M succinate buffer, pH 4.5. Immediately after adding the enzyme, the tempered ABTS solution was added. The sample was incubated for two minutes at the desired temperature, after which the absorbance was measured at the wavelength of 436 nm. In order for the added enzyme solution not to considerably decrease the temperature of the buffer, the volume of the enzyme added into the buffer in all dilutions was below 7% of the total volume. The dependence of the activity of the *M. albomyces* laccase on the temperature is shown in FIG. 4.

pH Optimum

Figure 5:
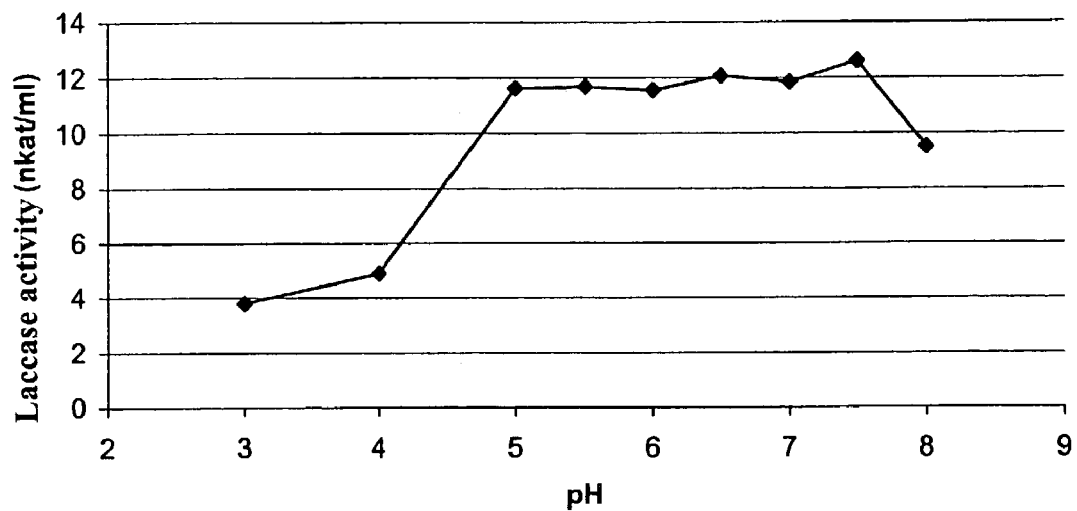
FIG. 5 shows the activity of the *M. albomyces* laccase at various pH values.

The pH optimum of the purified *M. albomyces* laccase was determined by measuring the laccase activity by the guaiacol method in McIlvaine buffer at pH values of 3, 4, 5, 6, 7 and 8. Guaiacol was selected because ABTS does not work when the pH is over 7. The enzyme was diluted into the buffers, and immediately after adding the enzyme, 25 µl of a 1% guaiacol solution was added. The reaction was followed for 5 minutes by a spectrophotometer at the wavelength of 465 nm. The dependence of the activity of the *M. albomyces* laccase on the pH is shown in FIG. 5.

Thermal Stability

Figure 6:
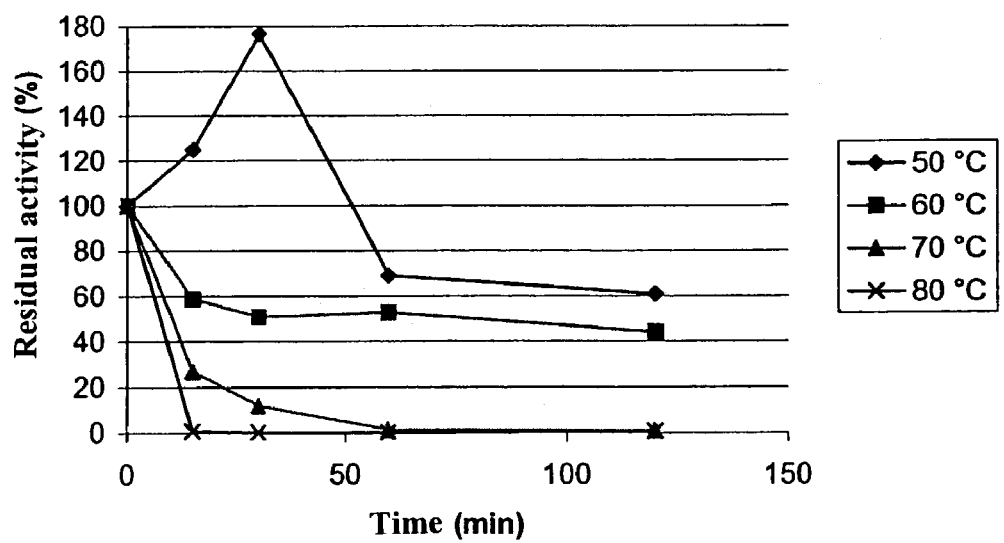
FIG. 6 shows the residual activity of the *M. albomyces* laccase at various temperatures.

The thermal stability of the *M. albomyces* laccase was determined by incubating the enzyme at 50, 60, 70 and 80° C. in 0.06 M citrate buffer, pH 6. The residual activity of the enzyme at each temperature was defined by the ABTS method after incubation of 15, 30, 60 and 120 minutes. The results of the thermal stability measurements are shown in FIG. 6.

Figure 7:
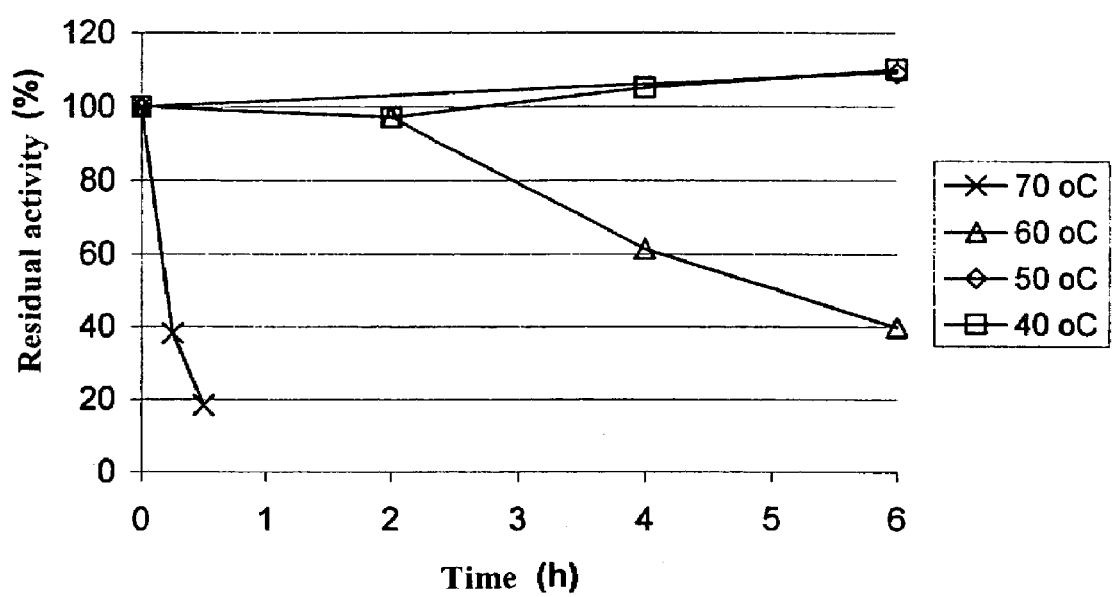
FIG. 7 shows the residual activity of a pure *M. albomyces* laccase at various temperatures.

The thermal stability of the purified *M. albomyces* laccase was determined in the conditions described above. The results are shown in FIG. 7. The results indicate that the residual activity of the enzyme remained essentially unchanged at 60° C. for as much as 2 hours. After 4 hours of incubation, there was still 60% residual activity left and after 6 hours, 40%.

pH Stability

Figure 8:
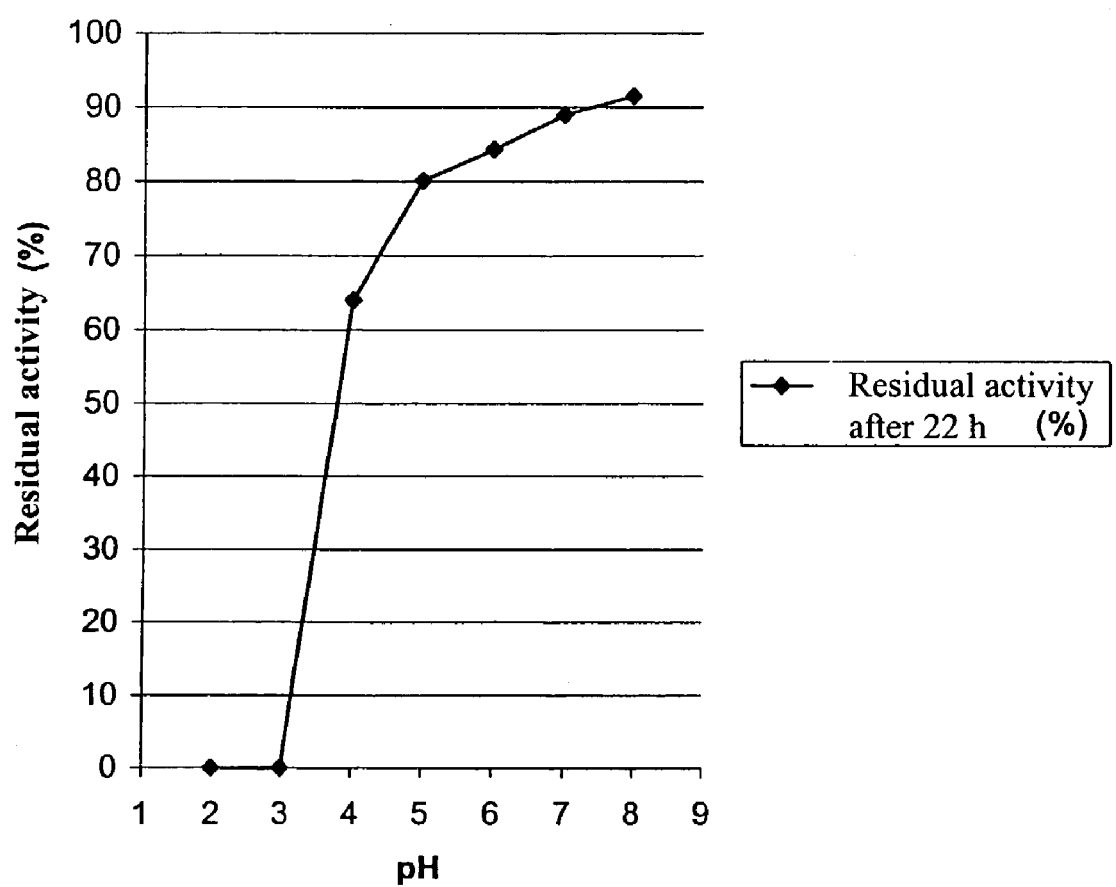
FIG. 8 shows the residual activity of the *M. albomyces* laccase at various pH values after 22-hour incubation.

The pH stability of the *M. albomyces* laccase was determined by incubating the enzyme at pH values 2, 3, 4, 5, 6, 7, and 8 in McIlvaine buffer at room temperature. The residual activity of the enzyme in the incubated samples at each pH was defined by the ABTS method after incubation of 1, 3, 5, and 22 hours. The results of the pH stability measurements are shown in FIG. 8.

Isoelectric Point

The isoelectric point of the *M. albomyces* laccase was determined by isoelectric focusing. The 0.5 mm thick polylacrylamide gel contained 7.5% acrylamide (Merck), 0.225% N,N'-bis-methyleneacrylamide (Merck), 6% ampholyte (Pharmalyte 2.5–5 for IEF, Pharmacia), 0.05% ammonium persulphate (Merck) and 0.05% N,N,N,N'-tetramethylene diamine (Merck). Isoelectric focusing was carried out using the Multiphor II electrophoresis equipment (Pharmacia LKB). The gels were stained using active dyeing, wherein the gel was dipped for about 10 seconds in a dilute ABTS solution (1 g/l). After about 15 minutes, the laccase bands appeared green. The pH distribution of the gel was determined using a pH surface electrode (Mettler Toledo). On the basis of isoelectric focusing, the isoelectric point of the *M. albomyces* laccase was 4.0.

EXAMPLE 4

Use of the *M. albomyces* Laccase in Oxidation of Dyes

Figure 9:
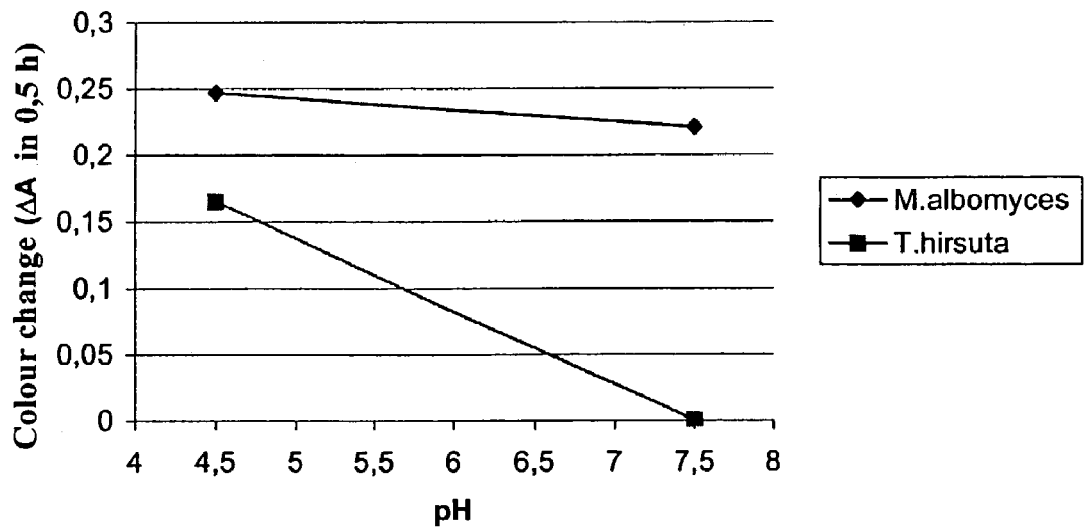
FIG. 9 shows the ability of *M. albomyces* and *T. hirsuta* laccases to form colour from 2,6-dimethoxyphenol at 40° C. at various pH values. The amount of laccase was 15 nkat/mmol of substrate.
Figure 10:
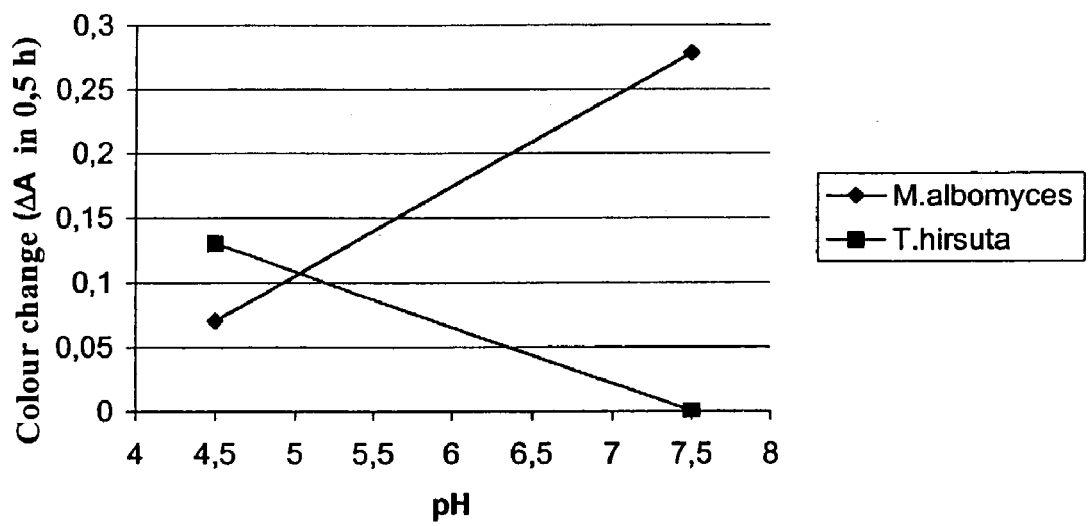
FIG. 10 shows the ability of the *M. albomyces* and *T. hirsuta* laccases to form colour from 2,6-dimethoxyphenol at 60° C. at various pH values. The amount of laccase was 30 nkat/mmol of substrate.
Figure 11:
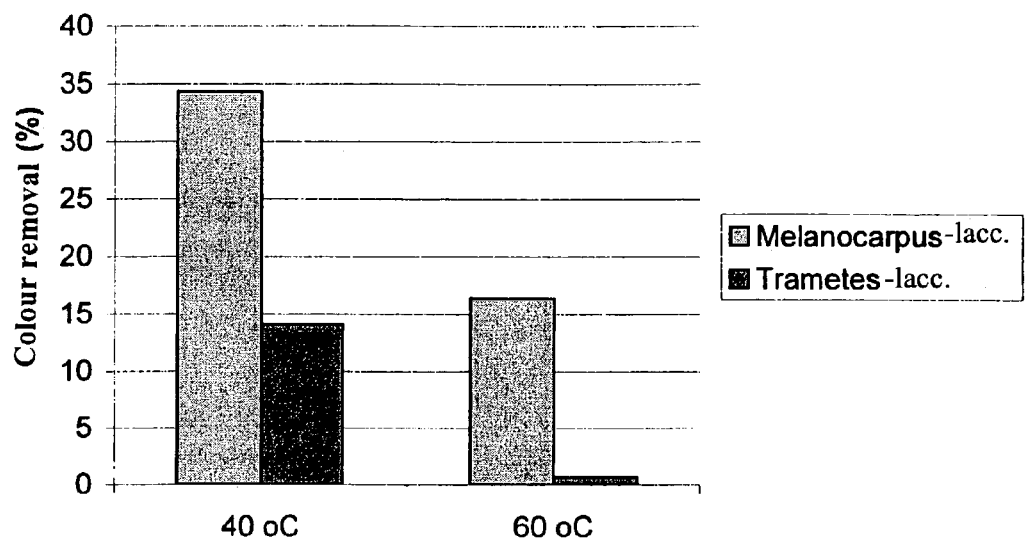
FIG. 11 shows the decolourisation of a textile dye under the effect of the *Melanocarpus* and *Trametes* laccases.

The tests were conducted by using a thermophilic *M. albomyces* laccase and the reference tests by a well-known laccase, which was isolated from *Trametes hirsuta* fungus. A conventional substrate, 2,6-dimethoxyphenol, was used as the substrate. The substrate concentration was 1 mmol/l, pH 4.5–7.5, and the temperatures 40 or 60° C. The amount of laccase was 15 nkat/g. The reaction mixtures were aerated during the test. At the end of the test (30 min), it was discovered that the thermophilic *M. albomyces* laccase worked better at a high temperature and pH, when the formation of colour from the dimethoxyphenol was measured at a wavelength of 468 nm (FIGS. 9 and 10).

Laccases can be used in removing colour from textile dyes. Laccases oxidize many dyes, which can be observed as colour removal. The colour removal of textile dyes was measured by using a dye commonly used in the textile industry, Diamond Black PLC. The laccase treatment was carried out at pH 7.5 and temperatures of 40 and 60° C. for 2 hours, the laccase dose being 20 nkat/mg of dye. On the basis of a maximum absorbance (560 nm) measurement, the *Melanocarpus* laccase removed 34% of the colour at 40° C. and 16% at 60° C., while the *Trametes* laccase only removed 14% at 40° C. and only 1% at 60° C. (FIG. 1).

The ability of the *M. albomyces* laccase to remove colour was compared with that of the *T. hirsuta* laccase at pH 5 and 8. The colour removal ability was studied using dyes commonly used in the textile industry. A colour solution (50 mg/l) was oxidized with a laccase dose of 1 nkat/ml in 50 mM succinate buffer (pH 5) or in a phosphate buffer (pH 8) for 24 hours at a temperature of 40° C. The colour removal was followed visually. The results are shown in Table 1. As the results indicate, both enzymes oxidized the tested dyes so that they turned colourless at pH 5. The *T. hirsuta* laccase was ineffective at pH 8, and did not oxidize the dyes tested, unlike the *M. albomyces* laccase, which even at pH 8 was able to oxidize the dyes. The results indicate that the behaviour of the *M. albomyces* laccase in oxidation of dyes is considerably more extensive than that of the conventional *Trametes* laccase.

TABLE 1

Removal of textile dyes with the *T. hirsuta* and the *M. albomyces* laccases at pH 5 and 8. (+ = colour removed from the solution, − = no colour removal from the solution)

| Dye | *T. hirsuta* laccase | | *M. albomyces* laccase | |
| --- | --- | --- | --- | --- |
| | pH 5 | PH 8 | pH 5 | pH 8 |
| Acid + metal complex dyes | | | | |
| Acid Blue 113 | + | − | + | + |
| Lanaset Blau 5G | + | − | + | + |
| After chrome dyes | | | | |
| Diamond Fast Brown | + | − | + | + |
| Diamant Schwarz PLC | + | − | + | + |

EXAMPLE 5

Use of the *M. albomyces* Laccase in Polymerisation

Figure 12:
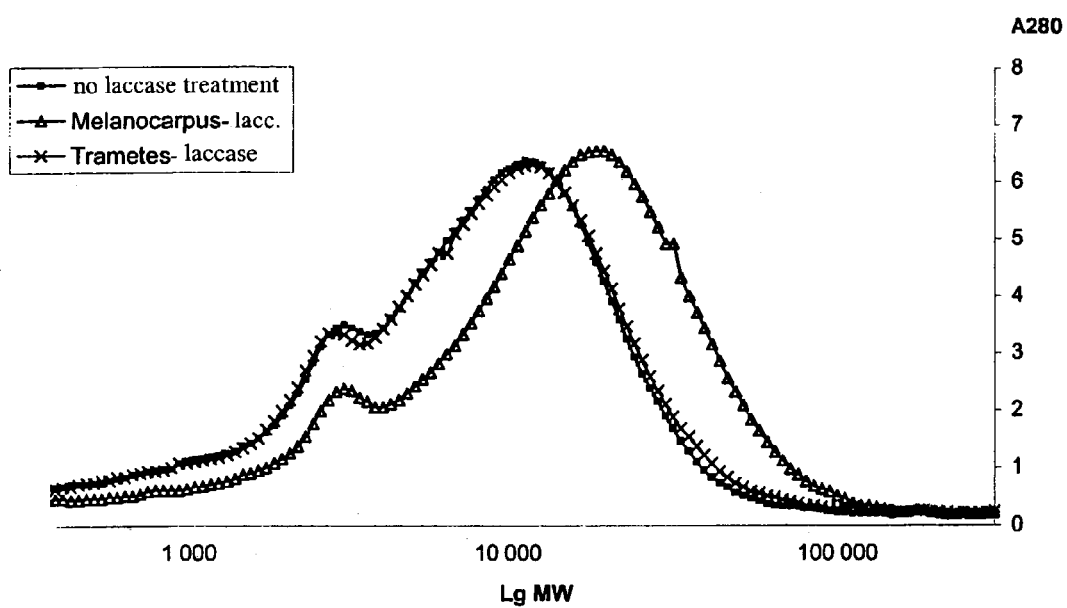
FIG. 12 shows the polymerisation of a lignin model substance under the effect of the *Melanocarpus* and *Trametes* laccases at 40° C.
Figure 13:
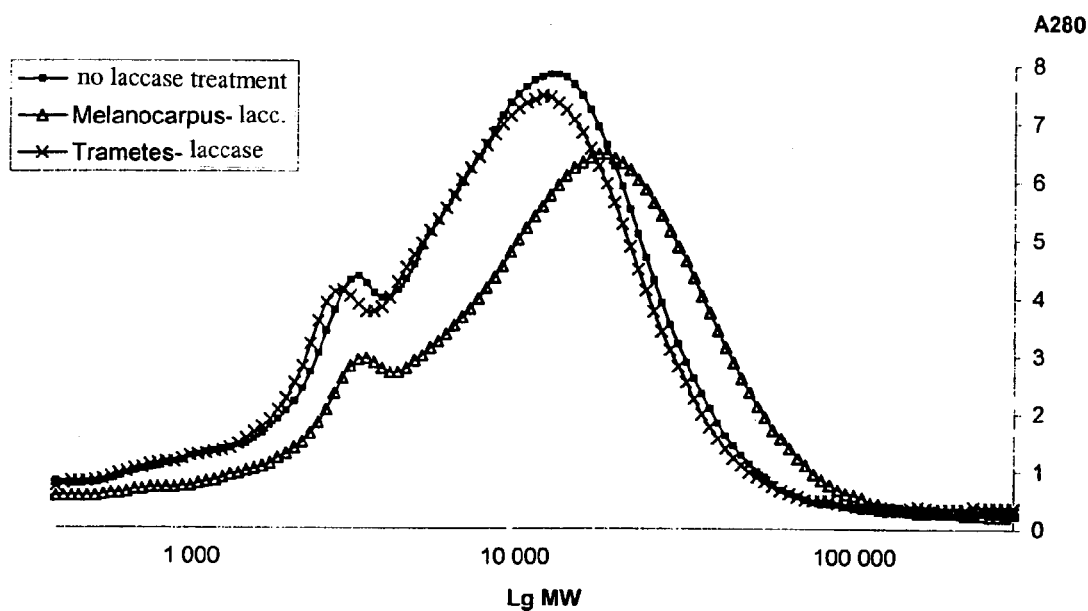
FIG. 13 shows the polymerisation of the lignin model substance under the effect of the *Melanocarpus* and *Trametes* laccases at 60° C.

The test studied the polymerisation of a model compound (lignin, Westvaco or Indulin AT, Sigma) with a thermophilic laccase. Lignin is a typical aromatic substrate of laccase. The reference tests were carried out using a laccase that had been isolated from *Trametes hirsuta*. The test conditions were as follows: substrate concentration 1%, pH 7.5, and temperatures 40 or 60° C. The amount of laccase was 200 nkat/g. The reaction mixtures were aerated during the test. The polymerisation was followed by determining the increase in the molecular weight of the polymerised lignin by GPC (gel permeation chromatography). At the end of the reaction (30 minutes), it was discovered that the thermophilic *M. albomyces* laccase worked more effectively than the reference laccase at a high temperature and pH. FIG. 12 illustrates a situation, wherein the polymerisation of lignin is carried out at 40° C. and, correspondingly, at 60° C. in FIG. 13. The *Melanocarpus* laccase causes an average increase in the molecular size and a decrease in the portion of small molecules obviously better than the *Trametes* laccase.

EXAMPLE 6

Use of the *M. albomyces* Laccase in Improving the Runnability of Paper Machines Laccase can be used to improve the runnability of paper machines by polymerising compounds originating in lignin and extractives and by decreasing the microbiological problems of the paper machine. Generally, the conditions of the paper machine are: the pH is 5–7 and the temperature 60–80° C. Treatment tests were conducted using a thermophilic and a conventional reference laccase in the paper machine conditions by using soluble compounds originating from lignin and extractives, isolated from the paper machine. The substrate concentration was 0.5% dry weight, the pH 7, and the temperature 70° C. Intensive agitation ensured sufficient oxygen content in the reaction. The reaction was monitored as the polymerisation of the aromatic and other compounds, which worked as the substrates of the laccase, by gel filtration (GPC). It was discovered that the reaction by the thermophilic *M. albomyces* laccase was more effective than by the reference laccase.

Figure 14:
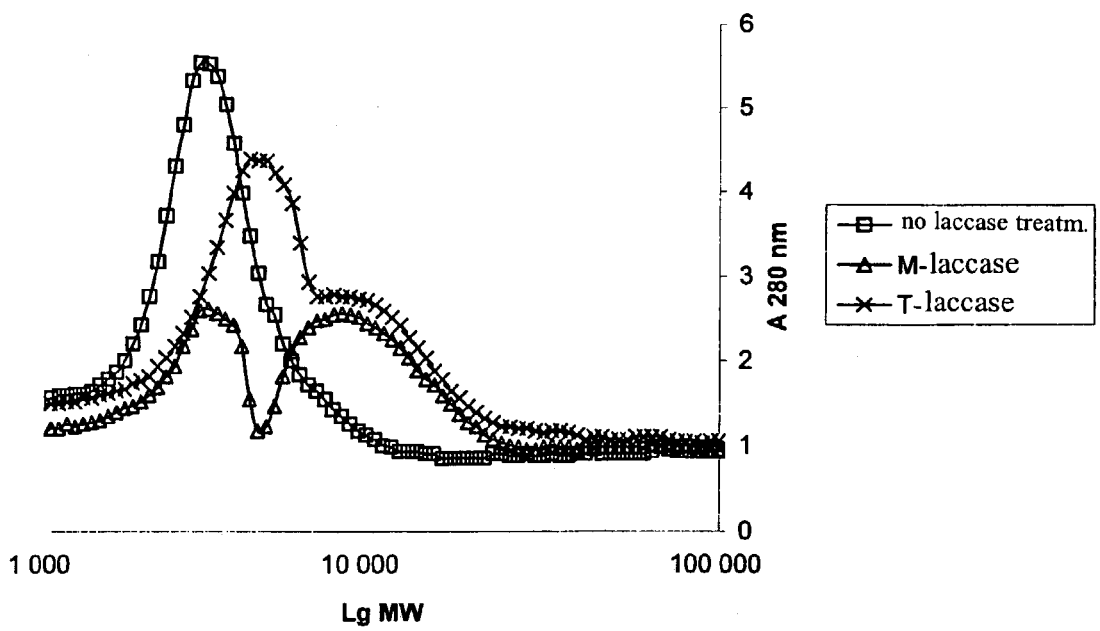
FIG. 14 shows the polymerisation of soluble compounds originating in lignin and extractives under the effect of the *Melanocarpus* and *Trametes* laccases at 70° C.

FIG. 14 shows how the *Melanocarpus* and *Trametes* laccases behave in the polymerisation of compounds originating from lignin and extractives at 70° C. In FIG. 14, the *Melanocarpus* laccase has clearly reduced the amount of small molecules.

EXAMPLE 7

Use of the *M. albomyces* Laccase in Oxidation of Fibres

Lignin-containing fibres, which were mechanically ground without chemical delignification, were treated with thermophilic *M. albomyces* laccase to activate and polymerise the lignin on the surface of the fibres. The treatments were conducted in the following conditions: the temperatures were 50 and 70° C., the pH 6, and the laccase concentration 200 nkat/g of fibres. The reaction mixture was aerated by blowing oxygen into the reaction mixture. The reference was a conventional laccase that was isolated from the *Trametes hirsuta* fungus. Hand sheets were prepared from the treated fibres. The physical properties of the sheets were measured. The results (Table 2) indicate that the density of the sheets made of the fibres treated with the *M. albomyces* laccase was clearly higher and the light scattering smaller than those of the reference sheets. No corresponding change was observed in sheets, which were made of fibres treated with the *T. hirsuta* laccase. The effect was especially obvious at an increased temperature of 70° C., wherein the *M. albomyces* laccase, because of its good thermal stability, behaved advantageously compared with the reference laccase that was isolated from the *T. hirsuta* fungus. On the basis of the result, it can be concluded that it was possible to use the *M. albomyces* laccase to polymerise lignin onto the surface of the fibres in the conditions used.

TABLE 2

The density and light scattering of the sheets made from fibres treated with the *M. albomyces* and *T. hirsuta* laccase

| Test | T (° C.) | Density (kg/m³) | Light scattering (m²/kg) |
|---|---|---|---|
| No enzyme | 70 | 339 | 55.0 |
| *T. hirsuta* laccase | 70 | 347 | 55.2 |
| *M. albomyces* laccase | 70 | 367 | 53.6 |

EXAMPLE 8

Use of the *M. albomyces* Laccase in Delignification of Fibres

Mediators can be used for expanding the substrate range of the laccase, among others, in delignification or other indirect oxidation of polymers. Hydroxybenzotriazole was selected as the mediator. Thermophilic laccase was used to degrade the lignin of kraft fibres in mediator-assisted oxidation. The reaction conditions were as follows: Kraft pulp, the kappa number about 29, the consistency 4%, the amount of mediator 1% of the pulp, the pH adjusted to 7, and the temperature 70° C., the reaction time 2 hours, the amount of laccase 500 nkat/g, in oxygen pressure (0.5 mPa). *Trametes* laccase served as a reference material. After the treatments, the pulps were subjected to alkali extraction, chelation, and one-stage peroxide bleaching. Dissolution of the lignin was monitored measuring the absorbance of the filtrate at a wavelength of 280 nm after alkali extraction. Handsheets were prepared of the pulps and ISO Brightness, and the kappa numbers were measured. As the results indicate (Table 3), the *M. albomyces* laccase works more effectively in the test conditions than the reference laccase; it decreased the kappa value of the sheets (the amount of lignin) and increased the absorbance$_{280nm}$ of the filtrate more than the reference laccase.

TABLE 3

The effect of LM treatment on the bleachability of kraft pulp (κ29) with an LQ-E-P sequence

| Test | A280 from filtrate | Kappa value |
|---|---|---|
| No enzyme | 11.9 | 18.9 |
| *T. hirsuta* laccase | 14.3 | 16.3 |
| *M. albomyces* laccase | 32.7 | 15.4 |

EXAMPLE 9

Isolation of the Gene and the cDNA of the *M. albomyces* Laccase

Total DNA was isolated from the cells according to Raeder and Broda (1985). A genomic library was constructed using a commercial reaction package (SuperCos I Cosmid Vector Kit, Stratagene), following the instructions of the manufacturer. 100 µg of DNA were partially cleaved with 5 U of a Sau3AI restriction enzyme (New England Biolabs) by incubating for 10 minutes at 37° C. The digested DNA was dephosphorylated with 20 U of CIAP (Calf Intestinal Alkaline Phosphatase, Finnzymes). The DNA molecules of different lengths were separated with a 15–30% sucrose gradient by ultracentrifugating for 22 hours at a temperature of 20° C. and a rotational speed of 22 000 rpm (the Beckman SW 41 TI rotor). The 12-ml sucrose gradient was divided into 300-µl fractions, and 10 µl of every second fraction were examined on 0.5% agarose gel by electrophoresis. The fractions, which on the basis of the gel electrophoresis contained DNA fragments of more than 20 kilobasepairs in length, were combined, and the DNA was precipitated from them with ethanol. The obtained DNA (about 2 µg) was inserted into SuperCos I cosmid vector (about 1 µg), which had been digested with XbaI (New England Biolabs), and thereafter dephosphorylated with CIAP and, finally, digested with BamHI (Boehringer Mannheim). Ligation was carried out with T4 DNA ligase (Promega) by incubating the mixture at 4° C. overnight. The ligation mixture was packed into λ particles by using a commercial reaction package (Gigapack III Gold packaging extract, Stratagene), following the instructions of the manufacturer, and the packed phage was used to infect *E. coli* host cells (the XL 1-Blue MR strain, Stratagene). One ligation provided more than 5×10⁶ clones, which can be considered a representative gene bank.

The hybridisation probe for the screening of the gene bank was obtained from the lac2 gene of the *Podospora anserina* fungus. This gene was selected as the probe, because the N-terminal amino acid sequence and the internal peptides of the *M. albomyces* laccase were homologous to the amino acid sequence of the *P. anserina* laccase. *P. anserina* fungus was grown on a substrate, which is described in FIG. 1. Genomic DNA was isolated from a mycelium, which was collected and freeze-dried after three days of growing, using a commercial reaction package (Easy DNA Kit, Invitrogen) in accordance with the manufacturer's instructions. The lac2 gene was multiplied by a PCR reaction, using primers that are based on the published sequence of the lac2 gene: 5'-TGCCACACTGCCGCCAACCGT-GCT-3' (SEQ ID NO: 3) (forward) and 5'-GTTCT-TGATATACCAATCAGGATG-3' (SEQ ID NO: 4) (reverse). The PCR program used for multiplication comprised 26 cycles, wherein the temperature program was as follows: denaturation of DNA at 94° C. for 45 seconds, insertion of primers at 55° C. for 1 min, extending the DNA chain with polymerase at 72° C. for 2.5 min. Finally, the chain was extended at 72° C. for 5 minutes. The obtained fragment of about 1.9 kilobasepairs in length was purified by agarose gel electrophoresis. Its behaviour as a probe was examined by Southern hybridisation with the genomic DNA of the *M. albomyces* fungus as follows: in two different reactions, 40 µg of DNA was cleaved with 80 U of EcoRI and HindIII restriction enzymes (New England Biolabs) at 37° C. for 5 hours. The fragments were separated by electrophoresis on 0.8% agarose gel; DNA was denatured and transferred onto Hybond N membranes (Amersham Pharmacia Biotech) (the method is described in Sambrook et al., 1989). The *P. anserina* lac2 gene was labelled with α-$^{32}$P-dCTP by using a commercial reaction package (Random primed DNA labelling kit, Boehringer Mannheim) in accordance with the manufacturer's instructions, and the bonding of the probe was examined at four different hybridisation temperatures: 48, 50, 55, and 60° C. The hybridisation solution contained 6×SSC, 1×Denhardt's (Sambrook et al., 1989), 0.5% SDS, and 100 µg/ml of Herring Sperm DNA (the SSC contains 0.15 M NaCl and 0.015 M sodium citrate at pH 7.0). The hybridisation contained about 5×10⁵ cpm/ml of labelled probe. After hybridisation, the membranes were washed in 2×SSC containing 0.1% SDS twice for five minutes at room temperature and, after this, for 30 minutes at the same temperature as the hybridisation was made at. The membranes were enclosed in an exposure cassette with a film, and the exposed film showed that the *P. anserina* lac2 gene was hybridised with a DNA fragment, which was about 4.5 kilobasepairs in length and cleaved with ExoRI enzyme.

About 5×10$^5$ clones from the obtained genomic gene bank were placed on agar plates, and colonies that had been growing overnight were transferred to nitrocellulose membranes (Protran, Schleicher & Schuell). The DNA contained by the colonies was denatured (Sambrook et al., 1989) and then attached to the membranes by heating at 80° C. for 2 hours. After the attachment of DNA, the residuals of the bacterial colonies were washed from the membranes by scrubbing them with the washing fluid (Sambrook et al., 1989) at 48° C. The DNA bound to the membranes was hybridised overnight at a temperature of 57° C. with a *P. anserina* lac2 gene that was labelled with α-$^{32}$P-dCTP (a hybridisation solution, as above). On the basis of the obtained hybridisation signals, several colonies were picked from the original plates, to which colonies the *P. anserina* lac2 gene had been hybridised. These colonies were further hybridised with the *P. anserina* lac2 gene and, on the basis of radioactive signals, 6 colonies were selected for further examination. Cosmids (Plasmid purification protocol, Tip-500, QIAGEN) were isolated from them. The restriction enzyme, which made it possible to isolate the laccase gene from the cosmid, was sought for by cleaving the cosmids with 19 different restriction enzymes. The obtained fragments were subjected to Southern hybridisation at a temperature of 57° C., using the *P. anserina* lac2 gene, as above. An EcoIRI fragment of about 4.5 kilobasepairs in length was again hybridised with the lac2 gene. The cosmid was cleaved with EcoRI, and the fragment was purified by agarose gel electrophoresis. The obtained fragment was inserted into plasmid pBluescriptSK⁻ (Stratagene), and the plasmid was transformed into *E. coli* host cells (strain DH5α, Gibco BRL) by electroporation. A clone was obtained from the transformation, containing the desired EcoRI fragment in pLLK1 plasmid. A laccase gene was sequenced from this plasmid, using synthesized oligonucleotide primers. The sequencing reactions were carried out using a commercial reaction package (DNA Sequencing Kit, dRhodamine Terminator Cycle Sequencing Ready Reaction, PE Biosystems) in accordance with the manufacturer's instructions.

To establish the introns contained by the *M. albomyces* laccase gene, a complementary DNA (cDNA) corresponding to the *M. albomyces* laccase was cloned by RACE-PCR, using a commercial reaction package (FirstChoice™ RLM-RACE Kit, Ambion, Inc.) in accordance with the manufacturer's instructions. RNA was isolated from the *M. albomyces* cells by a commercial reaction package (TRIZOL® Reagent, Life Technologies) in accordance with the manufacturer's instructions. The RNA was dephosphorylated and transcribed into DNA by using an inverse transcribing enzyme, whereafter the 5' and 3' ends of the gene were multiplied by separate PCR reactions in accordance with the manufacturer's instructions. The multiplication of both cDNA ends was carried out by two sequential PCR reactions using different primers. In the first reaction, the desired part of the laccase cDNA was multiplied using a gene-specific primer, and the second reaction ensured the multiplication of the laccase cDNA by using another gene-specific primer. In each PCR reaction, one of the primers needed for the multiplication of the DNA came from the RLM-RACE Kit reaction package, and it was bound to the adapter regions connected to the ends of the cDNA. The PCR program used for multiplication comprised 35 cycles, wherein the temperature program was as follows: denaturation of DNA at 94° C. for 30 seconds, insertion of primers at 60–62° C. for 30 sec, extension of DNA chain at 72° C. for 2 minutes. In the multiplication of the 5' end, the insertion temperature of the primers was 60° C., and in that of the 3' end, 62° C. Finally, chain extension was carried out at 72° C. for 7 minutes. The gene-specific primers used in the multiplication of the 5' end were as follows: in the first PCR reaction, 5'-GCCGGTGAGGATGTAGTCGATGAT-3' (SEQ ID NO: 5), and in the second reaction, 5'-AGGTGACGTTGAAC-CAGTAGTTGTC-3' (SEQ ID NO: 6). The gene-specific primers used in the multiplication of the 3' end were as follows: in the first PCR reaction, 5'-CTGGTGCACT-TCACGCAGAACAA-3'(SEQ ID NO: 7), and in the second reaction, 5'-AGAACCACTTCCAGGTGTCGCT-3'(SEQ ID NO: 8). From the RLM-RACE reactions, a fragment of 1194 basepairs in length was obtained from the 5' end, and from the 3' end, a fragment of 1322 basepairs in length. The fragments were isolated by agarose gel electrophoresis and cloned into a pCR2.1-TOPO™ vector by using a commercial reaction package (TOPO TA Cloning Kit, Invitrogen) in accordance with the manufacturer's instructions. The plasmid was transformed into *E. coli* host cells (strain TOP10F', Invitrogen) by using electroporation in accordance with the instructions of the reaction package. The cloned fragments were sequenced and the positions of the introns in the gene of the *M. albomyces* laccase were established by comparing the genomic sequence with the cDNA sequence obtained.

The genomic sequence of the gene is shown in FIG. 15. The introns are underlined.

REFERENCES

Altschul et al. 1990. *J. Mol. Biol.* 215, 403–410.

Berka et al. 1997. *Applied and Environmental Microbiology* 63(8):3151–3157.

Bharathi, M. S. and Ramalingam, K. 1993. *J. Anim. Morphol. Physiol.* 40(1&2):153.

Diamantidis et al. 2000. *Soil Biology & Biochemistry* 32: 919–927.

Fernandez-Larrea & Stahl. 1996. *Mol. Gen. Genet.* 252, 539–551.

Heinzkill et al. 1998. *Appl. Environ. Microbiol.* 64: 1601–1606.

Jönsson et al. 1997. *Curr. Genet.* 32: 425–430.

Laemmli 1970. *Nature* 27: 680–685.

Lowry et al. 1951. *J. Biol. Chem.* 193:265–275.

Kojima et al. 1990. *J. Biol. Chem.* 265: 15224–15230.

Niku-Paavola et al. 1988. *Biochem. J.* 254:877–884

Paszczynski et al. 1985. *FEMS Microbiol. Lett.* 29 (1985) 37–41 Ravanko, K. 1996. Termostabiilin lakkaasin seulonta (Screening of Thermostable Laccase). Master's Thesis. 97 p. 4 Appendices. (In Finnish)

Raeder and Broda, 1985. *Lett. Appl. Microbiol.* 1: 17–20.

Saloheimo et al. 1985. *J. Gen. Microbiol.* 137: 1537–1544.

Saloheimo and Niku-Paavola. 1991. *Bio/Technology* 9: 987–990.

Sambrook et al., 1989, *Molecular cloning: a laboratory manual,* 2nd. edn. Cold Spring Harbor Laboratory Press, Cold Spring Harbor, N.Y.

Yaver et al. 1996., *Appl. Environ. Microbiol.* 62: 834–841.

The invention claimed is:

1. An isolated enzyme, wherein:
   said isolated enzyme possesses a laccase activity.
   said isolated enzyme is isolated from the strains of the Melanocarpus genus, and
   wherein activity of the isolated enzyme is optimal at about pH 7.5 and the activity of the isolated enzyme is optimal at a temperature of about 70° C.

2. An isolated polypeptide, which has laccase activity, wherein said isolated polypeptide is encoded by a nucleic acid molecule selected from the group consisting of:
   a) a nucleic acid molecule comprising the coding region of SEQ ID NO:1;
   b) a nucleic acid molecule that encodes a polypeptide comprising an amino acid sequence according to SEQ ID NO:2;
   c) a nucleic acid molecule that differs from the nucleotide sequence SEQ ID NO:1 due to the degeneracy of the genetic code;
   d) a nucleic acid molecule which hybridizes to the nucleotide sequence of SEQ ID NO:1 under stringent conditions, wherein said stringent conditions comprise incubation in a hybridization solution comprising 6×SSC, 5×Denhardt's reagent, 0.5% SDS, 100 µg/ml denatured DNA at 68° C. or 6×SSC, 5×Denhardt's reagent, 0.5% SDS, 100 µg/ml DNA and 50% formamide at 42° C.; and
   e) a nucleic acid molecule that encodes a polypeptide wherein the amino acid sequence is at least 95% identical to SEQ ID NO:2.

3. An enzyme preparation, comprising: an isolated laccase enzyme, wherein said isolated laccase enzyme is produced by a recombinant
   host or strain comprising an expression vector, wherein said expression vector comprises
   a nucleic acid molecule encoding the polypeptide of claim 2.

4. The enzyme preparation according to claim 3, wherein the activity of the isolated enzyme is optimal at about pH 7.5 and the activity of the isolated enzyme is optimal at a temperature of about 70° C.

5. The enzyme preparation according to claim 3, wherein the isolated enzyme has a molecular weight of about 80 kDa as determined by SDS-PAGE.

6. An isolated polypeptide having laccase activity, wherein the isolated polypeptide has an amino acid sequence that is at least 99% identical to SEQ ID NO:2.

7. An enzyme preparation, comprising, as the main activity, the isolated polypeptide according to claims 2 or 6.

8. The enzyme preparation according to claim 7, farther comprising more than 10 mg/l of laccase enzyme.

9. The enzyme preparation according to 7, further comprising at least one additive.

* * * * *